United States Patent
Rutt et al.

(10) Patent No.: US 9,939,501 B2
(45) Date of Patent: Apr. 10, 2018

(54) ITERATIVE MINIMIZATION PROCEDURE WITH UNCOMPRESSED LOCAL SAR ESTIMATE

(71) Applicant: The Board of Trustees of the Leland Stanford Junior University, Palo Alto, CA (US)

(72) Inventors: Brian K. Rutt, Stanford, CA (US); Mihir R. Pendse, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 516 days.

(21) Appl. No.: 14/539,552

(22) Filed: Nov. 12, 2014

(65) Prior Publication Data

US 2016/0128574 A1    May 12, 2016

(51) Int. Cl.
| | |
|---|---|
| A61B 5/05 | (2006.01) |
| G01R 33/28 | (2006.01) |
| A61B 5/055 | (2006.01) |
| G01R 33/561 | (2006.01) |
| G01R 33/24 | (2006.01) |

(52) U.S. Cl.
CPC ............ *G01R 33/288* (2013.01); *A61B 5/055* (2013.01); *G01R 33/5612* (2013.01); *G01R 33/243* (2013.01); *G01R 33/246* (2013.01)

(58) Field of Classification Search
CPC ............ G01R 33/288; G01R 33/5612; G01R 33/246; G01R 33/243; A61B 5/055
See application file for complete search history.

(56) References Cited

U.S. PATENT DOCUMENTS

| | | | |
|---|---|---|---|
| 2003/0150476 A1 | 8/2003 | Suzuki | |
| 2008/0088305 A1* | 4/2008 | Olson | G01R 33/246 |
| | | | 324/309 |

(Continued)

FOREIGN PATENT DOCUMENTS

| | | |
|---|---|---|
| WO | WO 2013/169368 | 11/2013 |

OTHER PUBLICATIONS

Guerin et al. (Local SAR, global SAR, transmitter power and excitation accuracy trade-offs in low flip-angle parallel transmit pulse design) Magn Reson Med. Apr. 2014 ; 71(4): 1446-1457.*

(Continued)

*Primary Examiner* — Jennifer Dieterle
*Assistant Examiner* — Ellsworth Weatherby
(74) *Attorney, Agent, or Firm* — Beyer Law Group LLP

(57) ABSTRACT

A method for providing an image of a subject in a magnetic resonance imaging MRI system with parallel transmission (pTx) is provided. A localizer scan of the subject is provided. Body anatomy is determined from the localizer scan. The body anatomy is matched with at least one body model of a plurality of body models. $B_1^+$ and $B_o$ maps are calculated from the body anatomy. The electric fields from the at least one body model and constraints are used to simultaneously determine a plurality of excitation pulses for a pTx. MRI is performed on the subject using the determined excitation pulses. Global SAR is monitored in real time to ensure all time-averaged constraints are satisfied simultaneously.

15 Claims, 8 Drawing Sheets

(56) References Cited

U.S. PATENT DOCUMENTS

| | | | | |
|---|---|---|---|---|
| 2011/0043205 A1* | 2/2011 | Graesslin | ............ | G01R 33/5612 324/307 |
| 2015/0309147 A1* | 10/2015 | Schmitter | .............. | A61B 5/055 600/410 |
| 2015/0362574 A1* | 12/2015 | Wu | ..................... | G01R 33/4835 324/322 |

OTHER PUBLICATIONS

Hoyos-Idrobo, Andres, et al. "On variant strategies to solve the magnitude least squares optimization problem in parallel transmission pulse design and under strict SAR and power constraints." IEEE transactions on medical imaging 33.3 (2014): 739-748.*

Leeor Alon et al., "*A Method for Subject-Specific Body Model Generation using Affine and Non-Linear Transformations*," Proc. Intl. Soc. Mag. Reson. Med. 22 (2014) p. 0324.

William A. Grissom et al., "*Small-Tip-Angle Spokes Pulse Design Using Interleaved Greedy and Local Optimization Methods*," Magnetic Resonance in Medicine 68, pp. 1553-1562.

Yu No. Kiseliov, "*Algorithms of Projection of a Point Onto an Ellipsoid*," Lithuanian Mathematical Journal, vol. 34, No. 2, Apr.-Jun. 1994, pp. 141-159.

Krzysztof C. Kiwiel, "*A Method for Solving Certain Quadratic Programming Problems Arising in Nonsmooth Optimization*," IMA Journal of Numerical Analysis (1986) 6, pp. 137-152.

Angel Torrado-Carvajal et al., "*Automatic Segmentation Pipeline for Patient-Specific MRI Tissue Models*,". Proc. Intl. Soc. Mag. Reson. Med. 22 (2014), p. 4906.

Xiaotong Zhang et al., "*From Complex B1 Mapping to Local SAR Estimation for Human Brain MR Imaging Using Multi-Channel Transceiver Coil at 7T*," IEEE Transactions on Medical Imgaging, vol. 32, No. 6, Jun. 2013, pp. 1058-1067.

Simone Angela Winkler, et al., "*Direct SAR Mapping by Thermoacoustic Imaging: A Feasibility Study*," Proc. Intl. Soc. Mag. Reson. Med 22 (2014), p. 4898.

* cited by examiner

ITERATIVE MINIMIZATION PROCEDURE WITH UNCOMPRESSED LOCAL SAR ESTIMATE

GOVERNMENT RIGHTS

This invention was made with Government support under contract EB015891 and RR026351-01A1 awarded by the National Institutes of Health. The Government has certain rights in this invention.

BACKGROUND OF THE INVENTION

This invention relates generally to magnetic resonance imaging (MRI). More specifically, the invention relates to high field MRI.

SUMMARY OF THE INVENTION

In accordance with the invention a method for providing an image of a subject in a magnetic resonance imaging MRI system with parallel transmission (pTx) is provided. A localizer scan of the subject is provided. Body anatomy is determined from the localizer scan. The body anatomy is matched with at least one body model of a plurality of body models. $B_1^+$ and $B_o$ maps are calculated from the body anatomy. The electric fields from the at least one body model and constraints are used to simultaneously determine a plurality of excitation pulses for a pTx. MRI is performed on the subject using the determined excitation pulses. Global SAR is monitored in real time to ensure all time-averaged constraints are satisfied simultaneously.

The invention and objects and features thereof will be more readily apparent from the following detailed description and appended claims when taken with the drawings.

DETAILED DESCRIPTION OF ILLUSTRATED EMBODIMENTS

Figure 1:
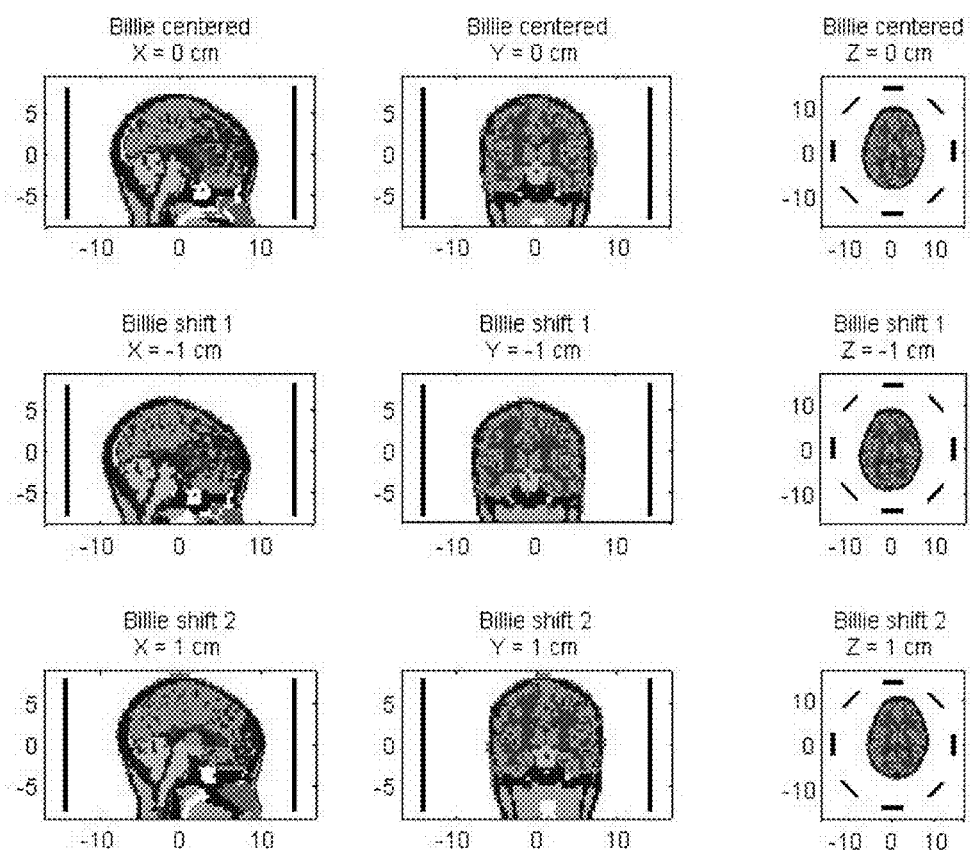
FIG. 1 shows three different positions of the Billie body model with the coil used for analysis of patient model mismatch.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Design of parallel transmit (pTx) RF pulses is ideally accomplished in real time, at the MR scanner, and yet in a manner that leads to control of local SAR or tissue heating. Recent work using local SAR estimates from numerical electromagnetic simulations during pulse design has the drawback of relying on a time-consuming compression step that overestimates peak local SAR to make the optimization tractable. In addition, most current methods fail to design all RF pulses in the sequence jointly despite the fact that local SAR constraints are time-averaged and therefore hotspots arising throughout the entire scan (and from all excited slices) are of interest rather than instantaneous SAR values for individual pulses. To address these issues, an embodiment of the invention introduces the minimum SAR formulation of the pTx pulse optimization problem and then describe the iterative minimization procedure with uncompressed local SAR estimate (IMPULSE), an efficient algorithm for solving it. The resulting pulses are guaranteed to satisfy strict criteria regarding excitation quality, patient safety, and hardware limits while still allowing for generality in the specific metrics used to define these criteria. Compared to existing approaches, improved scalability with regard to complexity of the safety constraints is demonstrated. In particular, not only is the need for compression of SAR matrices eliminated, but SAR matrices from arbitrarily many body models can be considered for increased robustness. Furthermore, we show that computation time scales favorably with number of total RF pulses due to algorithm's ability to parallelize the design of individual RF pulses while still using a single time-averaged safety estimate. Although a specific excitation scheme (slice-selective small-tip angle spokes trajectory) is described as a representative example to demonstrate the feasibility of designing an entire RF pulse sequence using a robust SAR estimate with practical computation times, other embodiments generalize the framework to incorporate arbitrary k-space trajectories, flip angle regimes, target excitation patterns, hardware constraints and safety criteria.

Ultra high field (UHF) MRI has several benefits, particularly those associated with the increased polarization of the nuclear spins; however, widespread adoption of UHF MRI is limited by flip angle inhomogeneity (FAI) and localized heating due to the increasingly complex interactions between the patient and the high-frequency transmitted electromagnetic fields. Parallel transmission (pTx), the intelligent design of RF waveforms for each channel of a multitransmit coil combined with manipulation of gradients/excitation k-space trajectory, has been proposed and experimentally demonstrated to be a promising method for achieving spatially-tailored excitation with acceptable levels of flip angle inhomogeneity (FAI).

Previous simulations have explored the design of pTx RF pulses with added patient safety constraints using numerical electromagnetic simulations on realistic body models to estimate electric fields and thereby specific absorption rate (SAR). These approaches make use of the SAR matrix formalism that allows computation of peak local SAR for arbitrary pTx pulses using a compact matrix notation. At UHF with shorter electromagnetic wavelengths, the resolution of the body model necessary to perform the electromagnetic simulation is such that typically greater than $10^5$ nonzero SAR matrices will result. Using generic optimization solvers, the time required for pTx pulse design becomes impractical when considering all SAR matrices; for this reason, the virtual observation point (VOP) compression method was developed as a pre-processing step, to allow the on-scanner real-time estimation of peak local SAR (over all uncompressed SAR matrices) in a way that guarantees no underestimation and bounded overestimation. Since the compression from the full set of SAR matrices to a much smaller set of VOP matrices requires a large computation time, it is typically pre-computed on each body model following the construction of SAR matrices from simulated electric fields.

The pulse design problem seeks to achieve desirable FAI while abiding by safety (local and global SAR) and hardware (instantaneous and time-averaged power) limits. Previous approaches cast the problem as a constrained minimization with FAI as the objective and SAR and power as constraints. To find the optimal pulse, one of the constraints, usually peak local SAR, is varied to generate an L-curve of FAI vs. peak local SAR. Then an optimal pulse is found by operating at the "knee" of this curve. Since all the constraints are quadratic, this problem can be made convex if the expression for the FAI is quadratic, which is the case if (a) the flip angle is in the small-tip regime, (b) the k-space trajectory is taken to be fixed and (c) the target phase of the excitation is taken to be fixed. However, relaxing these conditions is desirable: flexibility in the trajectory and target phase allows for additional reduction of FAI, and the desired flip angle may not satisfy the small-tip approximation. An algorithm for dealing with such nonconvexities efficiently is highly desirable.

One approach for preventing the formation of local SAR hotspots is through "SAR hopping" whereby each subpulse in the RF sequence deposits energy at a different spatial location, such that the time-averaged SAR map will have a peak SAR that is significantly lower than the sum of the peak SARs of each subpulse. Achieving SAR hopping requires that a single optimization be performed that considers the target excitation error of each slice independently but uses only one time-averaged SAR estimate for all RF pulses. Although an attempt has been made at achieving SAR hopping using VOPs and a single metric for FAI over all slices, there are two problems with this formulation. Firstly, because all slices are incorporated into a single FAI term, this can result in the undesirable situation where the FAI could be low because one slice is extremely homogeneous while another slice is quite inhomogeneous, resulting in poor image quality in most of the slices. It would be desirable to control the FAI of each slice separately to avoid this situation and ensure that all slices have acceptable homogeneity. The second problem results from the fact that a given VOP only estimates peak local SAR but not local SAR at each voxel. In other words, the SAR at a given voxel within a cluster corresponding to a particular VOP is taken to be the same as the peak SAR within that cluster. When that voxel does not correspond to the peak location within the cluster for a particular pulse, there will be additional error (beyond the overestimation error specified in the compression algorithm). Since the goal of SAR hopping is to have the hotspot location for one subpulse have low SAR on all other pulses, this source of error due to VOPS is especially problematic.

Another concern when trying to mitigate local SAR hotspots through pulse optimization involves the patient-specificity of the SAR estimate. When optimization is performed with an erroneous SAR estimate, the inadvertent creation of new hotspots and violation of regulatory limits (without knowing that they are being violated) is a real and troubling concern that motivates the development of more robust methods of local SAR estimation. One approach is to prepare a body model library and select a pre-computed SAR estimate based on the model that most closely matches the patient. However, since various conditions including position within the coil, overall shape and composition of the head, and presence of abnormalities (e.g. tumors) can affect SAR distributions, some degree of mismatch between patient and model will exist, leaving open the possibility of hotspots increasing rather than decreasing during the pulse optimization procedure. One way to add robustness to the estimate is to consider multiple body models/positions and computing peak local SAR over all models/positions. Unfortunately, in the VOP optimization framework, it would be necessary to compute the VOPs in real-time over the set of models/positions that were determined to match the patient which constitutes a time-consuming step. Alternatively, it would be possible to make an approximation of the compression by concatenating the precomputed VOPs for each model/position into a single set of VOP matrices, but this would result in an increase in the number of VOP matrices, leading to an increase in the computation time for optimization. Another approach is online patient-specific SAR estimation either through in-vivo SAR mapping or through numerical simulation applied to a custom individual-subject-based tissue model. These methods are able to produce electric fields in real-time which can then be used for SAR estimation. However, the need for real-time VOP compression again poses an additional costly step that would lengthen the duration of the scan.

An optimization algorithm that can incorporate several SAR terms in the computation (thus eliminating the need for VOPs) while also allowing joint design of all slices would be desirable in terms of (a) allowing for improved performance of SAR hopping, (b) allowing for a more robust SAR estimate by incorporating multiple body models and (c) reducing the computation time for VOP compression that is important for real-time SAR estimation methods. To this end, an embodiment introduces here a new pTx pulse design method, named iterative minimization procedure with uncompressed local SAR estimate (IMPULSE). This embodiment begins by introducing the minimum SAR formulation of the pulse design problem whereby all time-averaged safety and power metrics are incorporated into a single objective term to be minimized while being subjected to the constraint that each RF pulse must achieved the desired excitation patter to within some tolerance. Such a formulation allows for both SAR hopping (since all slices are being designed jointly) and for the specification of a strict tolerance on excitation error for every slice. FAI is expressed in its most general form without forcing the expression to be convex, thus allowing for adjustment of the excitation k-space trajectory and target phase throughout the optimization. To solve the minimum SAR problem, this embodiment introduces the IMPULSE method that allows this problem to be solved efficiently. IMPULSE uses the alternating direction method of multipliers (ADMM) to decouple the objective and constraints of the optimization problem in such a way that the complete minimum SAR problem can be solved by alternately and iteratively solving a SAR-dependent and an FAI-dependent step. The particular form of the SAR dependent step is such that a very large number of terms can be incorporated with negligible increase in computation time, eliminating the need for VOPs and allowing for the use of multiple models for SAR estimation. The FAI dependent step, despite being a non-convex procedure, has an efficient solution based on repeated projection of a point onto an ellipsoid. While this embodiment demonstrates IMPULSE here for the design of small-tip angle slice-selective pulses with a spokes trajectory, we discuss the straightforward extension and generalization of the algorithm to arbitrary excitation k-space trajectories, target excitation patterns, and large tip-angle regimes.

Theory

The following conventions will be used:

A tilde (e.g. b̃) denotes a concatenated vector corresponding to all RF pulses/slices A subscript in parenthesis denotes the pulse vector for the corresponding RF pulse/slice, so $b_{(s)}$ is the subvector of b corresponding to the sth RF pulse/slice. Specifically, $b_{(s)}$ is formed from elements $(s-1)N_K N_S + 1$ through $sN_K N_S$ of b̃.

A subscript without parenthesis refers to that element of the vector (e.g. $b_n$ is the nth element of b).

Bold font denotes a complex-valued quantity, regular font denotes a real-valued quantity.

A superscript refers to value of a variable at a given iteration. Parentheses refer to iterations of an outer loop of the algorithm while brackets refer to an inner loop. For example, $b^{(k)}$ refers to the value of b at the kth iteration of an outer loop and $b^{[j]}$ refers to the jth iteration of an inner loop (for an arbitrary iteration of the outer loop).

The elementwise matrix product is denoted by ∘.

When a vector is used in the argument of a function an element wise operation is assumed.

Vectors and matrices may be represented either in complex form or equivalent split-real form based on whether the particular operation or algorithm requires complex or real vectors.

The equivalent split-real form of a matrix A is $$A = \begin{bmatrix} Re\{A\} & -Im\{A\} \\ Im\{A\} & Re\{A\} \end{bmatrix}$$

and the equivalent split-real form of a vector b is $$B = \begin{bmatrix} Re\{A\} \\ Im\{A\} \end{bmatrix}.$$

In this way, the equivalent split-real form of c=Ab is c=Ab, so matrix multiplication is consistent with this notation. Bold/non-bold variables can be assumed to be equivalent complex/split-real forms of each other.

Minimum SAR Formulation

The minimum SAR optimization problem for design of homogeneous slice-selective small-tip RF pulses with a spokes trajectory under local SAR, global SAR, instantaneous power, and average power constraints is provided in an embodiment. We consider a multislice imaging sequence where numerous slices throughout the volume are to be excited and imaged, each requiring computation of an RF pulse. Slice-selectivity is accomplished through "spokes" along $k_z$ at discrete $k_x$-$k_y$ locations. The shape of the waveform to be played on each channel of the transmit coil during each spoke is identical and can be computed through conventional methods such as the Shinnar Le Roux algorithm based on the desired slice profile. The pulse design problem consists of determining the optimal spokes locations and complex weighting of the waveforms on each channel and each spoke that must be applied to achieve a homogeneous in-plane excitation profile while abiding by SAR and hardware constraints. We wish to determine a complex valued vector $\tilde{b} \in \mathbb{C}^{N_C N_K N_S}$ that specifies the complex (amplitude and phase) voltage to apply to each of $N_C$ transmit channels during each of $N_K$ spokes for each of $N_S$ different RF pulses/slices throughout the entire scan. We define $b_{(s)} \in \mathbb{C}^{N_C N_K}$ for $i=1, \ldots, N_S$ to be the individual pulse vector for the sth RF pulse. Due to the small-tip approximation, the transverse magnetization resulting from a given pulse $b_{(s)}$ can be characterized by a system matrix $F_{(s)} \in$ computed as $F = SYS(\mathbb{K}, B_{1,(s)}^+, \Delta B_{0,(s)})$ where $\mathbb{K}$ specifies the spoke locations, $B_{1,(s)}^+$ is the transmit RF magnetic field map for the given slice, $\Delta B_{0,(s)}$ is the static field deviation map for the given slice, and SYS represents the procedure to construct a system matrix. Since $B_{1,(s)}^+$ and $\Delta B_{0,(s)}$ are fixed but spokes locations can be optimized, the system matrix for a given spokes location can be expressed more compactly as $F_{(s)} = SYS_{(s)}(\mathbb{K})$. For many applications, the phase $\varphi_{(s)}$ of the excited transverse magnetization, $d_{(s)} = d_{mag,(s)} e^{i\varphi_{(s)}}$ is not important so an additional degree of freedom in optimization will result by specifying only the magnitude of the desired magnetization, $d_{mag,(s)}$ and allowing $\varphi_{(s)}$ to be variable. We can define the non-convex set of feasible pulses, $\mathcal{F}_{(s)}$, as the set of b that satisfy both the FAI and instantaneous power constraints: $\mathcal{F}_{(s)} = \bigcup_{\mathbb{K}, \varphi} \{b \| SYS_{(s)}(\mathbb{K})b - d_{mag,(s)} e^{i\varphi_{(s)}} \|_2 \leq \epsilon_{(s)}\} \cap \{b \| \|b\| \leq \psi_{inst}\}$ where $\psi_{inst}$ is the hardware limit on the amount of power that can be applied on one channel at any point in time. For fixed $\mathbb{K}$ and $\varphi$, the set is convex and is the intersection of an ellipsoid with a sphere. With variable $\mathbb{K}$ and $\varphi$, the resulting nonconvex set is the union of these convex sets. In this way, we can define $N_S$ independent sets of feasible pulses for each slice.

We now consider the following time-averaged constraints:

$$\text{Local SAR: } \frac{1}{N_S N_K} \sum_{s=1}^{N_S} \sum_{k=1}^{N_K} b_{(s)(k)}^H \left( \frac{Q_{local,v}}{\chi_{local}} \right) b_{(s)(k)} \leq 1 \text{ for } v = 1, \ldots, N_{SAR}$$

$$\text{Global SAR: } \frac{1}{N_S N_K} \sum_{s=1}^{N_S} \sum_{k=1}^{N_K} b_{(s)(k)}^H \left( \frac{Q_{global}}{\chi_{global}} \right) b_{(s)(k)} \leq 1$$

$$\text{Average Power: } \frac{1}{N_S N_K} \sum_{s=1}^{N_S} \sum_{k=1}^{N_K} b_{(s)(k)}^H \left( \frac{P_{ave,c}}{\psi_{ave}} \right) b_{(s)(k)} \leq 1 \text{ for } c = 1, \ldots, N_C$$

where $Q_{local,v}$ is the local SAR matrix for the with voxel of $N_{SAR}$ total voxels $\chi_{local}$ is the local SAR limit (e.g. 10 W/kg)

$Q_{global}$ is the global SAR matrix $\chi_{global}$ is the global SAR limit (e.g. 3.2 W/kg)

$P_{ave,c}$ is a matrix with all zeros except for the cth diagonal entry $\psi_{ave}$ is average power limit on each channel (e.g. 600 W)

Since peak local SAR, global SAR, and average power are all time-averaged metrics that scale proportionally with the RF duty cycle, they can all be expressed as a single cost function which is the maximum of $N_{SAR}+1+N_C$ terms:

$$\text{COST}(\tilde{b}) = \max_{r=1,\ldots,N_{SAR},c=1,\ldots,N_C} \left( \sum_{s=1}^{N_S} \sum_{k=1}^{N_K} b_{(s)(k)}^H \left( \frac{Q_{local,v}}{\chi_{local}} \right) b_{(s)(k)}, \right.$$

$$\left. \ldots \sum_{s=1}^{N_S} \sum_{k=1}^{N_K} b_{(s)(k)}^H \left( \frac{Q_{global,v}}{\chi_{global}} \right) b_{(s)(k)}, \sum_{s=1}^{N_S} \sum_{k=1}^{N_K} b_{(s)(k)}^H \left( \frac{P_{ave,c}}{\psi_{ave}} \right) b_{(s)(k)} \right)$$

Since $Q_{local,v}$, $Q_{global}$, and $P_{ave,c}$ are all positive semidefinite (PSD) matrices, for the purposes of optimization they can be interchanged, leading to the following simplified notation:

$$\text{COST}(\tilde{b}) = \max_{r=1,\ldots,N_R} \left( \sum_{s=1}^{N_S} \sum_{k=1}^{N_K} b_{(s)(k)}^H R_r b_{(s)(k)} \right)$$

Where $N_R = N_{SAR} + 1 + N_C$

The minimum SAR problem is:

MINIMIZE: $\text{COST}(\tilde{b})$

SUBJECT TO: $b_{(s)} \in \mathcal{F}_{(s)}$ for $s=1, \ldots, N_S$

We now consider the following time-averaged constraints:

Local SAR: $\frac{1}{N_S N_K} \sum_{s=1}^{N_S} \sum_{k=1}^{N_K} b_{(s)(k)}^H \left( \frac{Q_{local,v}}{\chi_{local}} \right) b_{(s)(k)} \leq 1$ for $v = 1, \ldots, N_{SAR}$ Global SAR: $\frac{1}{N_S N_K} \sum_{s=1}^{N_S} \sum_{k=1}^{N_K} b_{(s)(k)}^H \left( \frac{Q_{global}}{\chi_{global}} \right) b_{(s)(k)} \leq 1$ Average Power: $\frac{1}{N_S N_K} \sum_{s=1}^{N_S} \sum_{k=1}^{N_K} b_{(s)(k)}^H \left( \frac{P_{ave,c}}{\psi_{ave}} \right) b_{(s)(k)} \leq 1$ for $c = 1, \ldots, N_C$ where $Q_{local,v}$ is the local SAR matrix for the with voxel of $N_{SAR}$ total voxels $\chi_{local}$ is the local SAR limit (e.g. 10 W/kg)

$Q_{global}$ is the global SAR matrix $\chi_{global}$ is the global SAR limit (e.g. 3.2 W/kg)

$P_{ave,c}$ is a matrix with all zeros except for the cth diagonal entry $\psi_{ave}$ is average power limit on each channel (e.g. 600 W)

Since peak local SAR, global SAR, and average power are all time-averaged metrics that scale proportionally with the RF duty cycle, they can all be expressed as a single cost function which is the maximum of $N_{SAR}+1+N_C$ terms:

$$\text{COST}(\tilde{b}) = \max_{r=1,\ldots,N_{SAR},c=1,\ldots,N_C} \left( \sum_{s=1}^{N_S} \sum_{k=1}^{N_K} b_{(s)(k)}^H \left( \frac{Q_{local,v}}{\chi_{local}} \right) b_{(s)(k)}, \right.$$

$$\left. \ldots \sum_{s=1}^{N_S} \sum_{k=1}^{N_K} b_{(s)(k)}^H \left( \frac{Q_{global,v}}{\chi_{global}} \right) b_{(s)(k)}, \sum_{s=1}^{N_S} \sum_{k=1}^{N_K} b_{(s)(k)}^H \left( \frac{P_{ave,c}}{\psi_{ave}} \right) b_{(s)(k)} \right)$$

Since $Q_{local,v}$, $Q_{global}$, and $P_{ave,c}$ are all positive semidefinite (PSD) matrices, for the purposes of optimization they can be interchanged, leading to the following simplified notation:

$$\text{COST}(\tilde{b}) = \max_{r=1,\ldots,N_R} \left( \sum_{s=1}^{N_S} \sum_{k=1}^{N_K} b_{(s)(k)}^H R_r b_{(s)(k)} \right)$$

Where $N_R = N_{SAR} + 1 + N_C$

The minimum SAR problem is:

MINIMIZE: $\text{COST}(\tilde{b})$

SUBJECT TO: $b_{(s)} \in \mathcal{F}_{(s)}$ for $s=1, \ldots, N_S$

In this formulation, the peak local SAR, global SAR, and average power constraints are implicitly satisfied with the objective term $\text{COST}(\tilde{b})$ in the following way: Given an optimal pulse $\tilde{b}_{opt}$ that solves the above minimum SAR problem, the limiting constraint can be found by the term in $\text{COST}(\tilde{b}_{opt})$ that corresponds to the maximum (i.e. the r such that $\text{COST}(\tilde{b}_{opt}) = \tilde{b}_{opt}^H R_r \tilde{b}_{opt}$. All constraints can be guaranteed to be satisfied by selecting the maximum RF duty cycle such that this limiting constraint is satisfied. Although the objective $\text{COST}(\tilde{b})$ is convex, the constraint is non-convex in order to allow flexibility in the spokes locations and target phases leading to an increased ability to reduce FAI.

For a fixed target phase and spokes location, the FAI for the sth slice can be expressed as $\|\|F_{(s)}b - d_{(s)}\|\|_2$ in which case the problem is convex (specifically, it is a quadratically constrained quadratic program (QCQP)). The conventional approach for solving the minimum SAR problem would involve sequential quadratic programming (SQP) where at each iteration (1) the QCQP is solved with fixed target phase and spokes locations using a standard convex optimization solver to find the optimal pulse $\tilde{b}$, (2) the target phase is updated to match the phase excited by the optimal pulse, and (3) spokes locations are optimized to reduce the FAI with fixed target phase and $\tilde{b}$ using optimization transfer as in [1]. Unfortunately, when the total number of slices ($N_S$) and/or the total number of terms in the objective ($N_R$) is large, the speed of solving the QCQP with a generic interior-point or active set solver limits the total number of SQP iterations that can be performed in practice. For this reason one or more of the following approximations will likely have to be made using this approach:

VOP compression can be used to reduce the number of terms in the objective ($N_R$).

Each slice can be optimized independently (and in parallel) to reduce the size of the optimization variable and decrease computation time Spokes locations and/or target phase can be selected and fixed prior to the optimization Impulse An embodiment of the invention provides a way to eliminate all of these above approximations with a novel algorithm for solving this non-convex optimization problem. IMPULSE is based on the use of the alternating direction method of multipliers (ADMM) to decompose the problem in a way that exploits the independence of the $N_S$ excitation error constraints while still maintaining the coupling of the RF pulses in the objective term. The ADMM algorithm decomposes the optimization into sub-problems each of which consists of solving a smaller optimization problem. An embodiment provides efficient algorithms for these sub-problems that allow the total computation time to be short enough for real-time pulse design during a scan.

The derivation of the alternating direction method of multipliers is given in Appendix A. The general idea of the method is that when the objective can be expressed as the sum of multiple terms, it is possible to minimize each term independently while penalizing deviation from the optimum value found in the previous step. This procedure is done iteratively until some convergence criteria is reached. Specifically, the ADMM algorithm transforms problems of the form:

MINIMIZE: $v(x)+w(x)$ into

MINIMIZE: $v(y)+w(z)$

SUBJECT TO: $y=z$ and solves it with the following algorithm:

GIVEN: $k = 0$, $y^{(0)}$, $u^{(0)}$, $z^{(0)}$

REPEAT:

$$y^{(k+1)} = \mathrm{argmin}_y \left( v(y) + \frac{\rho}{2} \|y - z^{(k)} + u^{(k)}\|_2^2 \right)$$

$$z^{(k+1)} = \mathrm{argmin}_z \left( w(z) + \frac{\rho}{2} \|y^{(k+1)} - z + u^{(k)}\|_2^2 \right)$$

$$u^{(k+1)} = u^{(k)} + y^{(k+1)} - z^{(k+1)}$$

UNTIL: $|z^{(k+1)} - z^{(k)}| \le \epsilon_1$, $|z^{(k+1)} - y^{(k+1)}| \le \epsilon_2$ The $\rho$ parameter trades off the rate of convergence with the degree of sub-optimality of the solution. Larger values of $\rho$ correspond to fast convergence but high sub-optimality.

The ADMM algorithm can be applied to the minimum SAR problem by first expressing it as an unconstrained minimization:

MINIMIZE: $\mathrm{COST}(\tilde{b}) + \Sigma_{s=1}^{N_S} I_{(s)}(b_{(s)})$

Where $I_{(s)}$ is the indicator function for the set $$\mathcal{F}_{(s)}: I_{(s)}(b_{(s)})(b_{(s)}) = \begin{cases} 0, & b_{(s)} \in \mathcal{F}_{(s)} \\ \infty, & b_{(s)} \notin \mathcal{F}_{(s)} \end{cases}.$$

(This is a standard notational trick to express a constrained minimization as an unconstrained minimization: if $b_{(s)} \notin \mathcal{F}_{(s)}$, the value will be $\infty$ which is equivalent to a constraint being violated.) Now applying ADMM to the minimum SAR problem is straightforward by defining $v(\tilde{y}) = \mathrm{COST}(\tilde{y})$ and $w(\tilde{z}) = \Sigma_{s=1}^{N_S} I_{(s)}(b_{(s)})(z_{(s)})$. Thus the algorithm is:

GIVEN: $k = 0$; $y^{(0)}$, $u^{(0)}$, $z^{(0)}$

REPEAT: $\tilde{y}^{(k+1)} =$ $$\mathrm{argmin}_{\tilde{y}} \left( \max_{r=1,\ldots,N_R} \left( \sum_{s=1}^{N_S} \sum_{k=1}^{N_K} y_{(s)(k)}^H R_r y_{(s)(k)} \right) + \frac{\rho}{2} \|\tilde{y} - \tilde{z}^{(k)} + \tilde{u}^{(k)}\|_2^2 \right)$$

$$\tilde{z}^{(k+1)} = \mathrm{argmin}_{\tilde{z}} \sum_{s=1}^{N_S} I_{(s)}(z_{(s)}) + \frac{\rho}{2} \|\tilde{y}^{(k+1)} - \tilde{z} + \tilde{u}^{(k)}\|_2^2$$

$$\tilde{u}^{(k+1)} = \tilde{u}^{(k)} + \tilde{y}^{(k+1)} - \tilde{z}^{(k+1)}$$

UNTIL: $|\tilde{z}^{(k+1)} - \tilde{z}^{(k)}| \le \epsilon_1$, $|\tilde{z}^{(k+1)} - \tilde{y}^{(k+1)}| \le \epsilon_2$ The z-update can be further decomposed into $N_S$ independent (and parallelizable) operations:

$$z_{(s)}^{(k+1)} = \mathrm{argmin}_z \left( I_{(s)}(z) + \frac{\rho}{2} \|y_{(s)}^{(k+1)} - z + u_{(s)}^{(k+1)}\|_2^2 \right)$$

for $s = 1, \ldots, N_S$

This operation minimizes the deviation of the variable $z$ from $y_{(s)}^{(k+1)} + u_{(s)}^{(k+1)}$ while requiring that $z$ be a feasible pulse ($z \in \mathcal{F}_{(s)}$). In fact, the $\rho$ parameter becomes irrelevant and this step is equivalent to the Euclidean projection of the point $y_{(s)}^{(k+1)} + u_{(s)}^{(k+1)}$ onto the set $\mathcal{F}_{(s)}$:

$z_{(s)}^{(k+1)} = \mathrm{proj}\,\mathcal{F}_{(s)}(y_{(s)}^{(k+1)} + u_{(s)}^{(k+1)})$ for $s=1, \ldots, N_S$ So the complete ADMM algorithm for the minimum SAR problem is:

GIVEN: $k = 0$; $y^{(0)}$, $u^{(0)}$, $z^{(0)}$

REPEAT: $\tilde{y}^{(k+1)} =$ $$\mathrm{argmin}_{\tilde{y}} \left( \max_{r=1,\ldots,N_R} \left( \sum_{s=1}^{N_S} \sum_{k=1}^{N_K} y_{(s)(k)}^H R_r y_{(s)(k)} \right) + \frac{\rho}{2} \|\tilde{y} - \tilde{z}^{(k)} + \tilde{u}^{(k)}\|_2^2 \right)$$

(PARALLEL) FOR $$\tilde{z}_{(s)}^{(k+1)} = \mathrm{proj}_{\mathcal{F}_{(s)}}(y_{(s)}^{(k+1)} + u_{(s)}^{(k+1)})$$

for $s = 1, \ldots, N_S$

END FOR $$\tilde{u}^{(k+1)} = \tilde{u}^{(k)} + \tilde{y}^{(k+1)} - \tilde{z}^{(k+1)}$$

UNTIL: $|\tilde{z}^{(k+1)} - \tilde{z}^{(k)}| \le \epsilon_1$, $|\tilde{z}^{(k+1)} - \tilde{y}^{(k+1)}| \le \epsilon_2$ The y-update (or SAR update) is an unconstrained minimization of a (convex) piecewise quadratic function while the z-update (or FAI update) is a Euclidean projection of a point onto a non-convex set. Each of these subproblems can be solved with efficient algorithms that will now be described.

Algorithm for SAR Update

The SAR update is accomplished through Kelley's cutting plane algorithm which is a class of "bundle methods" for solving non-differentiable minimization problems. At each iteration $j$ a progressively more accurate piecewise linear underestimating approximator of $\mathrm{COST}(\tilde{y})$ called $\widetilde{\mathrm{COST}}^{[j]}$ $(\tilde{y}) = \max(G^{[j]T}\tilde{y} + w^{[j]})$ is constructed and $$\widetilde{\mathrm{COST}}^{[j]}(\tilde{y}) + \frac{\rho}{2}\|\tilde{y} - \tilde{z}^{(k)} + \tilde{u}^{(k)}\|_2^2,$$

which serves as a surrogate for $$\mathrm{COST}(\tilde{y}) + \frac{\rho}{2}\|\tilde{y} - \tilde{z}^{(k)} + \tilde{u}^{(k)}\|_2^2,$$

is minimized to find $\tilde{y}^{[j+1]}$. At each iteration we add another term to $\overline{COST}$ by adding a row to the matrix $G^{[j]}$ and an element to the vector $w^{[j]}$ based on the hyperplane that lies tangent to $COST(\tilde{y})$ at $\tilde{y}^{[j]}$. These can be found by evaluating both $COST(\tilde{y}^{[j]})$ and its subgradient, $g(\tilde{y}^{[j]})$. The use of the term sub-gradient rather than gradient is because $COST(\tilde{y})$ is piecewise quadratic which means that it is technically non-differentiable since at certain points there can be multiple tangent planes that pass through that point while underestimating the function. However, it is possible to find a sub-gradient at each point (i.e. at any point, it is possible to find at least one underestimating tangent plane through that point). Since the function $COST(\tilde{y})$ is constant across the outer ADMM iterations, the iteration counter of the $\tilde{y}$ updates is persistent across ADMM outer iterations in the sense that the value of $G^{[j]}$ and $w^{[j]}$ from the previous outer iteration can be stored and each new hyperplane can be appended to the existing approximation. In this way, after the first ADMM iteration, subsequent SAR updates take less time. The complete algorithm for the Kelley's cutting plane algorithm is:

GIVEN: $j, \tilde{z}^{(k)}, \tilde{u}^{(k)}, \tilde{y}^{[j]} = \tilde{z}^{(k)} - \tilde{u}^{(k)}, G^{[j]}, w^{[j]}$ REPEAT:
1. $[COST^{[j]}, g^{[j]}] = ORACLE(\tilde{y}^{[j]})$
2. Update the matrix $G^{[j]}$ by appending the vector $g^{[j]}$.
3. Update the vector $w^{[j]}$ by appending the entry $g^{[j]} - g^{[j]T}\tilde{y}^{[j]}$.
4. Update pulse by minimizing the surrogate function with the refined piecewise linear approximation:

$$\tilde{y}^{[j+1]} = \operatorname{argmin}_{\tilde{y}} \left( \max(G^{[j]T}\tilde{y} + w^{[j]}) + \frac{\rho}{2} \|\tilde{y} - \tilde{z}^{(k)} + \tilde{u}^{(k)}\|_2^2 \right)$$

UNTIL: COST stops changing

The two demanding steps in this procedure are Step 1, which involves evaluating the cost function and its sub-gradient, and Step 4, which involves performing the (convex) minimization of a piecewise linear function plus a quadratic term. The problem in Step 4 is a well-studied problem in the optimization literature and has an efficient algorithm described in [2]. Step 1 would normally be very expensive, but it is possible to construct an "oracle" that is able to accomplish this extremely efficiently. Both step 1 and step 4 require real-valued variables as inputs so all variables in the optimization are in their equivalent split-real form.

Vectorized SAR Oracle

An embodiment constructs an "oracle" that is queried with a point $\tilde{y}^{[j]}$ and returns the $COST^{[j]}$ and $g^{[j]}$. The oracle makes use of vectorized SAR computation that allows for simple GPU acceleration. While this new technique is especially important for this algorithm as the oracle must be queried numerous times throughout the course of the optimization, it is fundamentally more efficient than naive methods relying on "for loops", for computing time- and spatially-averaged local SAR for an entire pulse sequence with arbitrarily many voxels and RF pulses.

The general procedure to compute $COST^{[j]}$ and $w^{[j]}$ is:
1. Generate a $N_R$ element vector $p^{[j]}$ where the $r$ th element of $p^{[j]}$ is $\Sigma_{s=1}^{N_S} \Sigma_{k=1}^{N_K} b_{(s)(k)}^H R_r b_{(s)(k)}$
2. Find the value and index of the largest element of $p^{[j]}$: $[COST(\tilde{y}^{[j]}), r_{max}] = \max(p^{[j]})$
3. Compute a sub-gradient analytically: $g(\tilde{y}^{[j]}) = 2R_{r_{max}}\tilde{y}^{[j]}$ The most costly step is the first one and we describe a vectorized method to accomplish it efficiently that is orders of magnitude more efficient than using a "for loop". Not only is the vectorized method fundamentally more efficient in terms of total number of floating point operations needed, but because it expresses the computation as a matrix vector multiplication, there is an additional efficiency gain when using mathematical software that has built-in multithreading of matrix multiplication such as MATLAB. An added benefit is that because of MATLAB's built-in abstraction for using GPUs to multiply matrices (gpuArray), GPU acceleration can be achieved with no extra programming effort.

It is possible to exploit the symmetry of $R_r$ to evaluate $b_{(s)(k)}^H R_r b_{(s)(k)}$ in a minimal number of floating point operations as the inner product of two real valued vectors $R_{r,full}$ and $b_{(s)(k),full}$. Then $\Sigma_{s=1}^{N_S} \Sigma_{k=1}^{N_K} b_{(s)(k)}^H R_r b_{(s)(k)}$ can be computed efficiently as the inner product of $R_{r,full}$ and $b_{full} = \Sigma_{s=1}^{N_S} \Sigma_{k=1}^{N_K} b_{(s)(k),full}$. The entire vector $p^{[j]}$ can be constructed as a single matrix multiplication $R_{full}^T b_{full}$ where $R_{full}$ is a matrix with the $r$th column equal to $R_{r,full}$.

The expressions for $R_{r,full}$ and $b_{(s)(k),full}$ are found by expanding $b_{(s)(k)}^H R_r b_{(s)(k)}$. For simplicity, we will drop the subscripts and use the notation $x^H S x$ in the derivation where single subscripts indicate vector elements and double subscripts indicate matrix elements.

$$\sum_{i=1}^{N_c}\sum_{j=1}^{N_c} S_{ij} x_i^* x_j = \sum_{i=1}^{N_c} S_{ii}|x_i|^2 + \sum_{i=1}^{N_c}\sum_{j=1}^{i}(S_{ij}x_i^* x_j + S_{ij}^* x_i x_j^*)$$

$$= \sum_{i=1}^{N_c} S_{ii}|x_i|^2 + 2\sum_{i=1}^{N_c}\sum_{j=1}^{i} \operatorname{Re}\{S_{ij} x_i^* x_j\}$$

$$= \sum_{i=1}^{N_c} S_{ii}|x_i|^2 + 2\sum_{i=1}^{N_c}\sum_{j=i+1}^{N_c}(\operatorname{Re}\{S_{ij}\}\operatorname{Re}\{x_i^* x_j\} - \operatorname{Im}\{S_{ij}\}\operatorname{Im}\{x_i^* x_j\})$$

It can be seen that the above expression can be written as the inner product of two real valued vectors $\hat{S}, \hat{x} \in \mathbb{R}^{N_c^2}$ $$\hat{S} = \begin{bmatrix} S_{1,1} \\ \vdots \\ S_{N_c,N_c} \\ 2\operatorname{Re}\{S_{12}\} \\ -2\operatorname{Im}\{S_{12}\} \\ \vdots \\ 2\operatorname{Re}\{S_{1,N_c}\} \\ -2\operatorname{Im}\{S_{1,N_c}\} \\ \vdots \\ \vdots \\ 2\operatorname{Re}\{S_{N_c-1,N_c}\} \\ -2\operatorname{Im}\{S_{N_c-1,N_c}\} \end{bmatrix}$$

-continued and $$\hat{x} = \begin{bmatrix} |x_1|^2 \\ \vdots \\ |x_{N_C}|^2 \\ \text{Re}\{x_1^*x_2\} \\ \text{Im}\{x_1^*x_2\} \\ \vdots \\ \text{Re}\{x_1^*x_{N_C}\} \\ \text{Im}\{x_1^*x_{N_C}\} \\ \vdots \\ \text{Re}\{x_{N_C-1}^*x_{N_C}\} \\ \text{Im}\{x_{N_C-1}^*x_{N_C}\} \end{bmatrix} = \begin{bmatrix} \text{Re}\{x_1\}^2 \\ \vdots \\ \text{Re}\{x_{N_C}\}^2 \\ \text{Re}\{x_1\}\text{Re}\{x_2\} \\ -\text{Im}\{x_1\}\text{Re}\{x_2\} \\ \vdots \\ \text{Re}\{x_1\}\text{Re}\{x_{N_C}\} \\ -\text{Im}\{x_1\}\text{Re}\{x_{N_C}\} \\ \vdots \\ \text{Re}\{x_{N_C-1}\}\text{Re}\{x_{N_C}\} \\ -\text{Im}\{x_{N_C-1}\}\text{Re}\{x_{N_C}\} \end{bmatrix} + \begin{bmatrix} \text{Im}\{x_1\}^2 \\ \vdots \\ \text{Im}\{x_{N_C}\}^2 \\ \text{Im}\{x_1\}\text{Im}\{x_2\} \\ \text{Re}\{x_1\}\text{Im}\{x_2\} \\ \vdots \\ \text{Im}\{x_1\}\text{Im}\{x_{N_C}\} \\ \text{Re}\{x_1\}\text{Im}\{x_{N_C}\} \\ \vdots \\ \text{Im}\{x_{N_C-1}\}\text{Im}\{x_{N_C}\} \\ \text{Re}\{x_{N_C-1}\}\text{Im}\{x_{N_C}\} \end{bmatrix} =$$

$$\begin{bmatrix} 1 \\ \vdots \\ 1 \\ 1 \\ -1 \\ \vdots \\ 1 \\ -1 \\ \vdots \\ 1 \\ -1 \end{bmatrix} \circ \begin{bmatrix} \text{Re}\{x_1\} \\ \vdots \\ \text{Re}\{x_{N_C}\} \\ \text{Re}\{x_1\} \\ \text{Im}\{x_1\} \\ \vdots \\ \text{Re}\{x_1\} \\ \text{Im}\{x_1\} \\ \vdots \\ \text{Re}\{x_{N_C-1}\} \\ \text{Im}\{x_{N_C-1}\} \end{bmatrix} \circ \begin{bmatrix} \text{Re}\{x_1\} \\ \vdots \\ \text{Re}\{x_{N_C}\} \\ \text{Re}\{x_2\} \\ -\text{Re}\{x_2\} \\ \vdots \\ \text{Re}\{x_{N_C}\} \\ -\text{Re}\{x_{N_C}\} \\ \vdots \\ \text{Re}\{x_{N_C}\} \\ -\text{Re}\{x_{N_C}\} \end{bmatrix} + \begin{bmatrix} \text{Im}\{x_1\} \\ \vdots \\ \text{Im}\{x_{N_C}\} \\ \text{Im}\{x_1\} \\ \text{Re}\{x_1\} \\ \vdots \\ \text{Im}\{x_1\} \\ \text{Re}\{x_1\} \\ \vdots \\ \text{Im}\{x_{N_C-1}\} \\ \text{Re}\{x_{N_C-1}\} \end{bmatrix} \circ \begin{bmatrix} \text{Im}\{x_1\} \\ \vdots \\ \text{Im}\{x_{N_C}\} \\ \text{Im}\{x_2\} \\ \text{Im}\{x_2\} \\ \vdots \\ \text{Im}\{x_{N_C}\} \\ \text{Im}\{x_{N_C}\} \\ \vdots \\ \text{Im}\{x_{N_C}\} \\ \text{Im}\{x_{N_C}\} \end{bmatrix}$$

In this way it is possible to write $x^H S x$ as $\hat{S}^T$ (sgn○(x[inds1]○x[inds2])+x[inds3]○x[inds4]) where ○ is the elementwise product, sgn is a $N_c^2$ element vector consisting of −1 and 1; inds1, inds2, inds3, and inds4 are $N_c^2$ element vectors consisting of integers denoting indices of elements of x so x[inds1], x[inds2], x[inds3], and x[inds4] are $N_c^2$ element vectors consisting of components of x.

Therefore, it can be seen that the matrix $R_{full} \in \mathbb{R}^{N_c^2}$ can be constructed with each column computed as above for a particular $R_r$. Each $b_{(s)(k),full}$ is also computed as above for a particular $\tilde{b}$. It is possible to pre-compute $P_{full}$, sgn, inds1, inds2, inds3, and inds4 offline. In real time, to evaluate $p^*$ for a particular $\tilde{b}^*$, the following computations are necessary:

1. Generate $b_{(s)(k)}$ for all s, k by reshaping $\tilde{b}$ into a $N_C \times N_S N_K$ real-valued matrix $b_{reshape}$ whose $((s-1)N_K+k)$th column is $b_{(s)(k)}$. This involves first converting $\tilde{b}$ into a real-valued vector with twice the size by interleaving real and imaginary components and then reshaping. Since Step 4 in the SAR update requires b to be real-valued the input to the SAR oracle will be real-valued in which case this conversion step can be eliminated and therefore this first step involves only reshaping, which takes negligible amount of time.

2. Generate $b_{(s)(k)}$[inds1], $b_{(s)(k)}$[inds2], $b_{(s)(k)}$[inds3], and $b_{(s)(k)}$[inds4], for all s, k. This involves accessing elements of the variable $b_{reshape}$ at predetermined indices to form four new $N_C^2 \times N_S N_K$ matrices $b_{reshape}$[inds1], $b_{reshape}$[inds2], $b_{reshape}$[inds3], and $b_{reshape}$[inds4] whose respective whose $((s-1)N_K+k)$th columns are $b_{(s)(k)}$[inds1], $b_{(s)(k)}$[inds2], $b_{(s)(k)}$[inds3], and $b_{(s)(k)}$[inds4]. This operation only requires accessing an existing matrix at predefined locations and thus requires zero floating point operations and takes a negligible amount of time.

3. Compute $b_{(s)(k),full}$ for all s, k. This can be done calculating a matrix $b_{reshape,full}$: $b_{reshape,full}$=(sgn○(b_{reshape}[inds1]○b_{reshape}[inds2])+b_{reshape}[inds3]○b_{reshape}[inds4]). This requires three elementwise matrix products and one matrix addition, each done $N_S N_K N_C^2$ times. Of these, the elementwise matrix products, the one with the sgn takes negligible amount of time, so this step has 3 floating point matrix computations and $3 N_S N_K N_C^2$ total FLOPs.

4. Compute $b_{full} = \sum_{s=1}^{N_S} \sum_{k}^{N_K} b_{(s)(k),full} = b_{reshape,full} 1$. This requires 1 matrix operation and a total of $(N_S N_K - 1) N_{CF}^2$ FLOPs.

5. Compute matrix multiplication $R_{full}^T b_{full}$. This requires 1 multiplications and $N_P(N_C^2 - 1)$ additions for a total of $N_P(2N_C^2 - 1)$ FLOPs Total number of FLOPs: $3N_S N_K N_C^2 + (N_S N_K - 1) + N_P(2N_C^2 - 1) = N_C^2(3N_S N_K + 2N_P) + N_S N_K - N_P - 1 \approx N_C^2(3N_S N_K + 2N_P)$ In comparison, to naively compute p* with a "for loop" and computing the quadratic form directly requires $3N_R N_S N_K N_C^2$ complex operations or $18 N_R N_S N_K N_C^2$ total FLOPs. When $2N_P >> 3N_S N_K$ the vectorized computation takes approximately $2N_C^2 N_P$ FLOPs and which makes it $9N_S N_K$ times faster than the "for loop". In practice, with software such as MATLAB with built-in multithreading, especially when using a GPU, the number of matrix operations is a better comparison for computation time because matrix operations can be performed in approximately constant time. In this case the vectorized formulation has only 5 matrix operations whereas "for loop" method requires $2N_R N_S N_K$ matrix operations.

Algorithm for FAI Update

The FAI update consists of projection onto a nonconvex set. This projection operation can be accomplished through iterative projections onto the convex set formed by fixing the phase and spokes locations while updating the phase and spokes locations after each projection:

GIVEN $\mathbb{K}_{(i)}^{[0]} = \mathbb{K}_{(i)}^{(k)}, F_{(i)}^{[0]} = F_{(i)}^{(k)}$
and $d_{(i)}^{[0]} = d_{(i)}^{(k)}$

REPEAT

1. $z_{(s)}^{[j]} = \text{proj}_{\mathcal{F}_{convex,(s)}^{[j-1]}}(y_{(s)}^{(k+1)} + u_{(s)}^{(k)})$
2. $d_{(s)}^{[j]} = d_{mag,(s)} e^{i\angle(F_{(s)}^{[j-1]} z_{(s)}^{[j]})}$
3. $F_{(s)}^{[j]} = \text{SYS}(\text{argmin}_\mathbb{K}(\|\text{SYS}_s(\mathbb{K}) z_{(s)}^{[j]} - d_{(s)}^{[j]}\|)$
4. $\mathcal{F}_{convex,(s)}^{[j]} = \{z | \|F_{(s)}^{[j-1]} z - d_{(s)}^{[j]}\|_2 \leq \epsilon_{(s)}$ and $|z_n|^2 \leq \psi_{inst}$ n=1, ..., $N_C N_K\}$ UNTIL: $z_{(s)}^{[j]}$ stops changing.

Since the convex set $\mathcal{F}_{convex,(s)}^{[j]}$ is an intersection of an ellipsoid (not centered at the origin) and a sphere centered at the origin, the projection onto this set can be accomplished through the method of alternating projections onto convex sets. An efficient algorithm for the projection onto an ellipsoid is described in reference [3] and projection onto the centered sphere is done trivially by normalizing the vector by an appropriate scale factor. Step 2 involves finding the target phase that minimizes the FAI with fixed pulse and spokes locations. This is exactly equal to the phase of the excited magnetization with the given pulse and spokes locations. Step 3 involves finding the spokes locations that minimize the FAI with fixed pulse and target phase and updating the system matrix based on those new locations. This cannot be done exactly but an approximate solution is found through optimization transfer as described in [1].

Methods

To demonstrate the performance of the algorithm, RF pulses will be designed for the Billie body model of the Virtual Family with simulated B1+ and E field maps using an 8-channel loop array head coil with a coil diameter, strip width, and strip length of 28.5 cm, 5.0 cm, and 16 cm, respectively. Several test cases will be analyzed to assess the performance of IMPULSE. In many cases comparisons will be made with optimization done using sequential quadratic programming (SQP) with VOPs. The algorithm for the SQP used for comparison is:

GIVEN: $k=0$, $\mathbb{K}_{(s)}^{(0)}, F_{(s)}^{(0)}, d_{(s)}^{(0)}, d_{mag,(s)}$ REPEAT:
1. $\tilde{b} = OPT_{cnvx}(\mathcal{F}_{convex,(1)}^{[j]}, \ldots, \mathcal{F}_{convex,(N_S)}^{[j]})$
2. $d_{(s)}^{[j]} = d_{mag,(s)} e^{i\angle(F_{(s)}^{[j]} z_{(s)}^{[j]})}$
3. $F_{(s)}^{[j]} = SYS(\operatorname{argmin}_{\mathbb{K}} (\|SYS_s(\mathbb{K})z_{(s)}^{[j]} - d_{(s)}^{[j]}\|))$
4. $\mathcal{F}_{convex,(s)}^{[j]} = \{z | \|F_{(s)}^{[j-1]} z - d_{(s)}^{[j]}\|_2 \leq \epsilon_{(s)}$ and $|z_n|^2 \leq \psi_{inst}$ $n=1, \ldots, N_C N_K\}$ UNTIL: COST stops changing Here, $OPT_{cnvx}$ indicates the solving of a convex optimization problem with a generic solver taken as a black-box. We use the MOSEK ((MOSEK ApS, Copenhagen Denmark) solver for our results. The particular formulation of this convex problem depends on the particular case being analyzed and will be described in more detail. Depending on the case, Step 3 may or may not be performed.

In our analysis we will vary three aspects of the optimization: jointness of problem, degree of non-convexity, and robustness of body model.

Jointness of Optimization Slices:

JOINT (Solve one joint problem):

MINIMIZE: COST($\tilde{b}$)

SUBJECT TO: $b_{(s)} \in \mathcal{F}_{(s)}$ for $s=1, \ldots, N_S$

INDEPENDENT (Solve $N_S$ independent problems in parallel):

For $s=1, \ldots, N_S$:

MINIMIZE: COST($b_{(s)}$)

SUBJECT TO: $b_{(s)} \in \mathcal{F}_{(s)}$

The ideal situation is for the problem to be solved jointly to allow for SAR hopping, but this comes at the cost of computation time because the size of the optimization variable increases by a factor of $N_S$.

Degree of Non-Convexity:

VARIABLE $\varphi$, FIXED $\mathbb{K}$ $$\mathcal{F}_{(s)} = \bigcup_{\varphi,\mathbb{K}} \{b \mid \|F_{(s)} b - d_{(s)} \circ e^{i\varphi}\|_2 \leq \epsilon_{(s)}\} \cap \{b \mid |b|^2 \leq \psi_{inst}\}$$

$$= \left\{\bigcup_{\varphi} \mathcal{F}_{ellip,(s)}(\varphi)\right\} \cap \mathcal{F}_{norm,(s)}$$

VARIABLE $\varphi$, VARIABLE $\mathbb{K}$ $$\mathcal{F}_{(s)} = \bigcup_{\varphi,\mathbb{K}} \{b \mid \|SYS_s(\mathbb{K})b - d_{(s)} \circ e^{i\varphi}\|_2 \leq \epsilon_{(s)}\} \cap \{b \mid |b|^2 \leq \psi_{inst}\}$$

$$= \left\{\bigcup_{\varphi,\mathbb{K}} \mathcal{F}_{ellip,(s)}(\varphi, \mathbb{K})\right\} \cap \mathcal{F}_{norm,(s)}$$

Allowing $\varphi$ and/or $\mathbb{K}$ to be variable allows for more degrees of freedom in decreasing FAI but at the cost of an increasingly non-convex problem.

Robustness of SAR Estimate

| Single model/VOP: | |
| --- | --- |
| Index of cost function | Safety or Hardware Metric |
| 1 | Local SAR estimated at |
| ... | each of $N_{VOP, 1}$ |
| $N_{VOP, 1}$ | virtual observation points in first (and only) body model |
| $N_{VOP, 1} + 1$ | Global SAR in first (and only) body model |
| $N_{VOP, 1} + 2$ | Average power on each of |
| ... | $N_C$ channels |
| $N_{VOP, 1} + N_C$ | |

| Single model/uncompressed: | |
| --- | --- |
| Index of cost function | Safety or Hardware Metric |
| 1 | Local SAR at each of |
| ... | $N_{SAR, 1}$ voxels in first |
| $N_{SAR, 1}$ | (and only) body model |
| $N_{SAR, 1} + 1$ | Global SAR in first (and only) body model |
| $N_{SAR, 1} + 2$ | Average power on each of |
| ... | $N_C$ channels |
| $N_{SAR, 1} + N_C$ | |

| Multiple models/VOP: | |
| --- | --- |
| Index of cost function | Safety or Hardware Metric |
| 1 | Local SAR estimated at |
| ... | each of $N_{VOP, 1}$ |
| $N_{VOP, 1}$ | virtual observation points in first of M body models |
| ... | ... |
| $N_{VOP, 1} + \cdots + N_{VOP, M-1} + 1$ | Local SAR at each of $N_{VOP, M}$ virtual |
| ... | observation points in last |
| $N_{VOP, total} = N_{VOP, 1} + \cdots + N_{VOP, M}$ | of M body models |
| $N_{VOP, total} + 1$ | Global SAR in first of M body models |
| ... | ... |
| $N_{VOP, total} + M$ | Global SAR in last of M body models |
| $N_{VOP, total} + M + 1$ | Average power on each of |
| ... | $N_C$ channels |
| $N_{VOP, total} + M + N_C$ | |

| Multiple models/IMPULSE: | |
|---|---|
| Index of cost function | Safety or Hardware Metric |
| 1 | Local SAR at each of |
| ... | $N_{SAR,\ 1}$ voxels in first of M |
| $N_{SAR,\ 1}$ | body models |
| ... | ... |
| $N_{SAR,\ 1} + \cdots$ | Local SAR at each of |
| $N_{SAR,\ M-1} + 1$ | $N_{SAR,\ M}$ voxels in last of M |
| ... | body models |
| $N_{SAR,\ total} = N_{SAR,\ 1} + \cdots + N_{SAR,\ M}$ | |
| $N_{SAR,\ total} + 1$ | Global SAR in first of M |
| | body models |
| ... | ... |
| $N_{SAR,\ total} + M$ | Global SAR in last of M |
| | body models |
| $N_{SAR,\ total} + M + 1$ | Average power on each of |
| ... | $N_C$ channels |
| $N_{SAR,\ total} + M + N_C$ | |

Additional terms in the cost function allow for more robust SAR estimation but come at a computational cost. The Billie model with its brain centered in the coil is taken to represent the reference and true SAR estimate. The Billie model shifted by 1 cm anteriorly, superiorly, and to the right is taken to be the first mismatched model and the Billie model shifted by 1 cm posteriorly, inferiorly, and to the left is taken to be the second mismatched model. For all body models, VOPs were computed using the standard VOP compression algorithm. The overestimation parameter, ε, in the VOP algorithm was set to 2.5% of the worst case SAR. This resulted in 1065 VOPs for the centered model, 853 VOPs for the first shifted model, and 675 VOPs for the second shifted model.

Initialization

Both IMPULSE and SQP methods require initial spokes locations and target phases to be found such that the feasible set is nonempty. The approach used for initialization is to perform (in parallel for each slice independently) interleaved greedy and local pulse design with only regularization of total pulse power and no local SAR information. The $\lambda_{(s)}$ parameter in this optimization should be chosen based on the specified FAI tolerance $\in_{(s)}$ such that the pulse resulting from the interleaved greedy and local has an FAI that is as close to the specified tolerance (deviation from the specified tolerance indicates sub-optimality in the selected spokes locations). Empirically, it was found that $\lambda_{(s)} = 5\in_{(s)}$ is a reasonable choice. At the end of this step, it may be that the tolerance is still not met. In this case, additional magnitude-least-square (MLS) iterations are performed with fixed number of spokes while decreasing λ at each iteration until the FAI tolerance is satisfied.

Effect of Optimizing 𝕂

To analyze the improvement obtained by allowing 𝕂 to vary vs. fixing it in terms of computation time, the following problem (called cases 1 and 2) was solved using both IMPULSE and SQP: case 1-$\in_{(s)}$=10%; single, perfectly matched body model; joint optimization; fixed 𝕂, variable φ, excited slices at z=−2.5 cm and z=+5 cm case 2-$\in_{(s)}$=10%; single, perfectly matched body model; joint optimization; variable 𝕂 and φ, excited slices at z=−2.5 cm and z=+5 cm.

Analysis of IMPULSE Algorithm

To demonstrate general aspects of the IMPULSE algorithm including selection of the ρ parameter, duration of SAR and FAI updates, and overall reduction of SAR vs. time, the results from case 2 was used.

Effect of Jointness

To analyze the ability to achieve SAR hopping by formulating the problem as a joint optimization, the following problem (called case 3) was solved using both IMPULSE and SQP and compared to case 2: case 3-$\in_{(s)}$=10%; single, perfectly matched body model; independent optimization; variable 𝕂, variable φ, excited slices at z=−2.5 cm and z=+5 cm.

Effect of Mismatch

To analyze the error resulting from body model mismatch the following problem (called cases 4 and 5) was solved using both IMPULSE and SQP and compared to case 2: case 4-$\in_{(s)}$=10%; single mismatched body model, shifted-Billie 1; joint optimization; variable 𝕂, variable φ, excited slices at z=−2.5 cm and z=+5 cm; case 5-$\in_{(s)}$=10%; single mismatched body model, shifted-Billie 2; joint optimization; variable 𝕂, variable φ, excited slices at z=−2.5 cm and z=+5 cm. FIG. 1 shows three different positions of the Billie body model with the coil used for analysis of patient model mismatch.

Correction of Mismatch

To demonstrate the correction of mismatch error by using multiple models, the following problem (called case 6) was solved using both IMPULSE and SQP and compared to cases 2, 4 and 5: case 6-$\in_{(s)}$=10%; two mismatched body models, shifted-Billie 1 and shifted-Billie 2; joint optimization; variable 𝕂, variable φ, excited slices at z=−2.5 cm and z=+5 cm.

Scaling of IMPULSE with Number of Slices

To demonstrate the ability of IMPULSE to design pulses jointly for very large numbers of slices, the following problem (called case 7) was solved using only IMPULSE (it is computationally intractable to solve this using SQP): case 6-$\in_{(s)}$=5%; single matched body model; joint optimization; variable 𝕂, variable φ, 100 excited slices from z=−5 cm to z=+7 cm.

Summary:

| Case # | Jointness of Optimization | Degree of nonconvexity | Body model | # of slices |
|---|---|---|---|---|
| 1 | Joint | Variable φ | Single matched | 2 |
| 2 | Joint | Variable φ and 𝕂 | Single matched | 2 |
| 3 | Independent | Variable φ and 𝕂 | Single matched | 2 |
| 4 | Joint | Variable φ and 𝕂 | Single mismatched 1 | 2 |
| 5 | Joint | Variable φ and 𝕂 | Single mismatched 2 | 2 |
| 6 | Joint | Variable φ and 𝕂 | Multiple mismatched | 2 |
| 7 | Joint | Variable φ and 𝕂 | Single matched | 100 |

Results

Effect of Optimizing 𝕂

Figure 2:
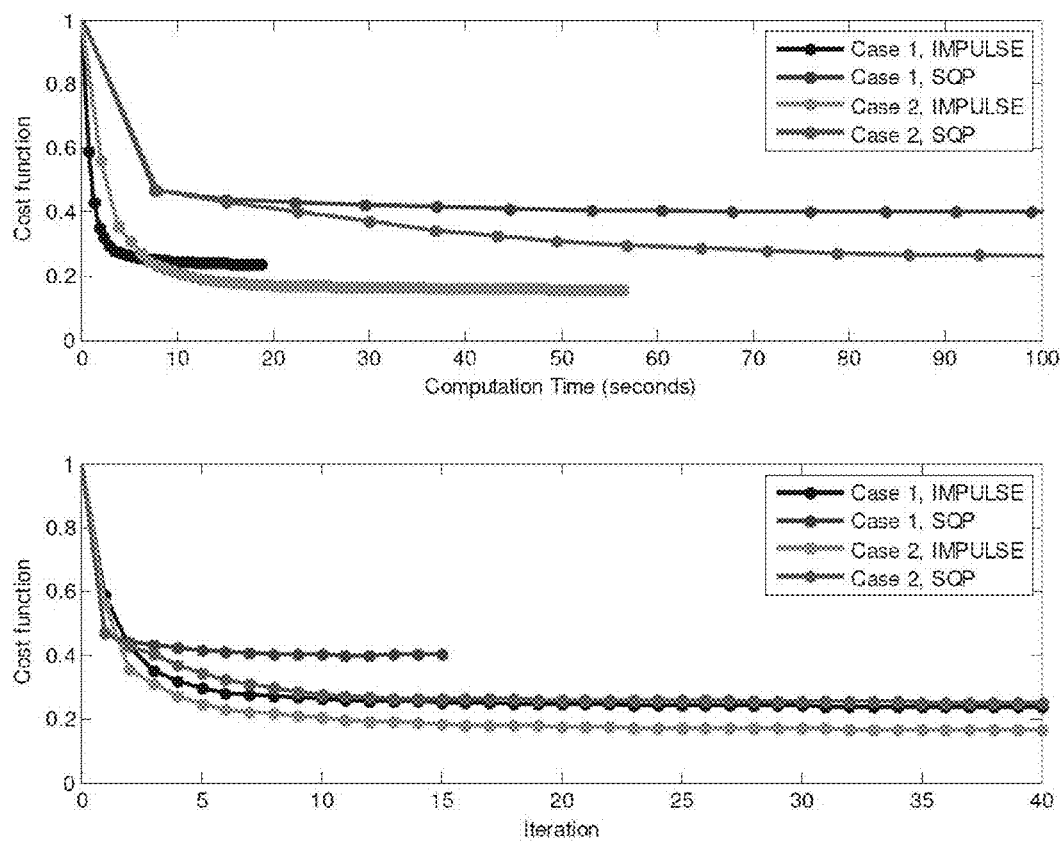
FIG. 2 indicates that allowing spokes locations to be optimized results in a significant reduction in the value of the cost function regardless of whether SQP or IMPULSE is used.

FIG. 2 indicates that allowing spokes locations to be optimized results in a significant reduction in the value of the cost function regardless of whether SQP or IMPULSE is used. Unfortunately, when using SQP, optimizing spokes locations comes at a relatively greater cost in computation time compared to IMPULSE. The reason for this is that many more iterations are required for convergence when 𝕂 is allowed to vary compared to when 𝕂 is fixed. Because the duration of each iteration for IMPULSE is less than for SQP, the increase in number of iterations results in a smaller increase in absolute computation time for IMPULSE compared to SQP.

Figure 3:
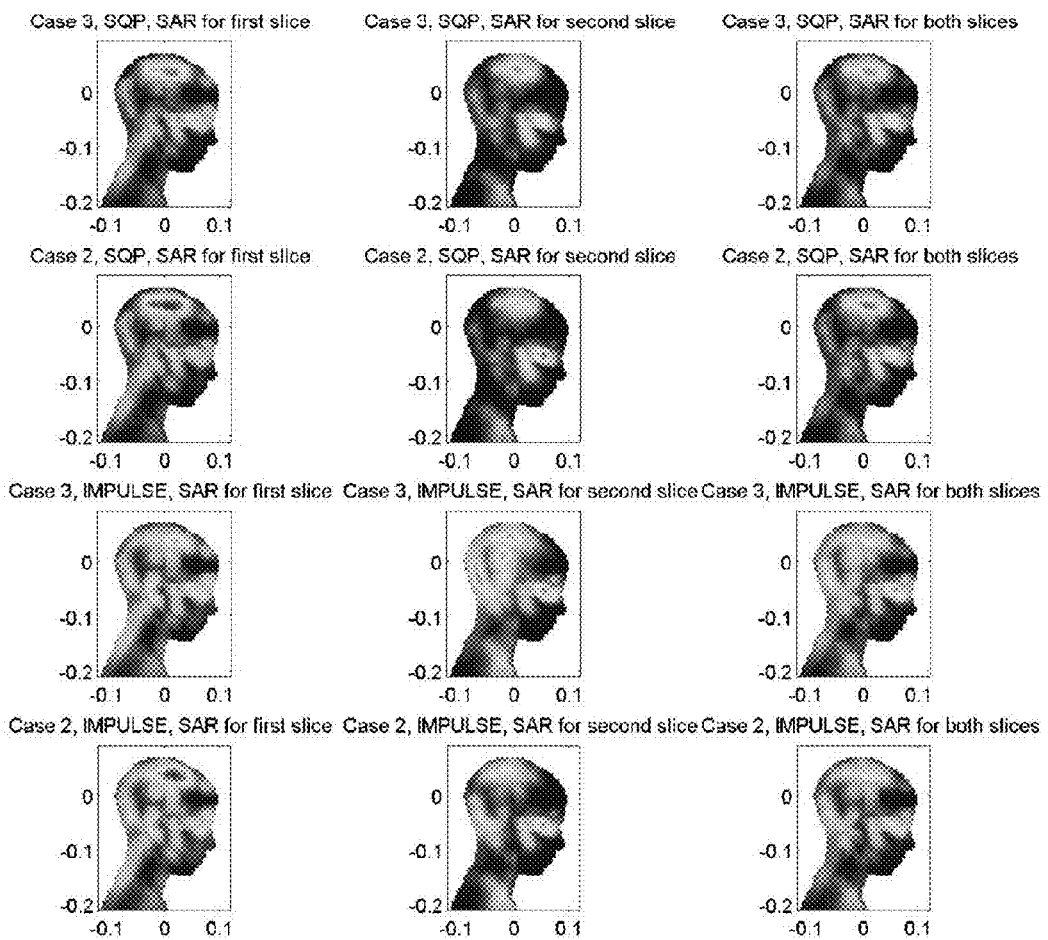
FIG. 3 illustrates the effect of designing slices jointly versus independently with both IMPULSE and SQP.

FIG. 3 illustrates the effect of designing slices jointly versus independently with both IMPULSE and SQP. The benefit of IMPULSE compared to SQP in terms of achieving SAR hopping is evident in the FIG. 3. With IMPULSE, using independent optimization, a hotspot near the eyes is present. When using IMPULSE with joint optimization, this hotspot is suppressed. With SQP, performance is inherently poor because of the hotspot near the top of the head. Using joint optimization shows limited ability to suppress this.

Figure 4:
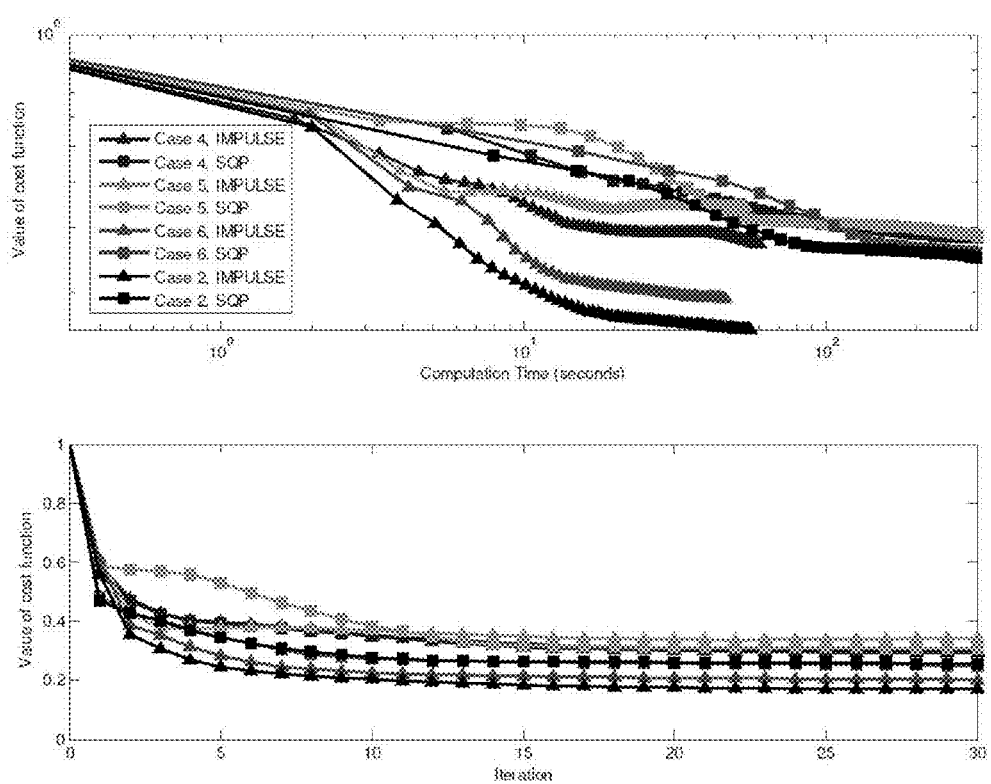
FIG. 4 illustrates error optimization due to patient model mismatch and correction through the use of multiple models.

FIG. 4 illustrates error optimization due to patient model mismatch and correction through the use of multiple models. In FIG. 4, cases 4 and 5 demonstrate that the use of a mismatched body model for the SAR estimate results in a greater value of the cost function after convergence. This can be partially remedied by using multiple mismatched body models. This method works using both SQP and IMPULSE, but because SQP scales poorly with total number of VOP terms, this approach results in a significant increase in computation time with SQP but negligible increase in computation time with IMPULSE.

Figure 5:
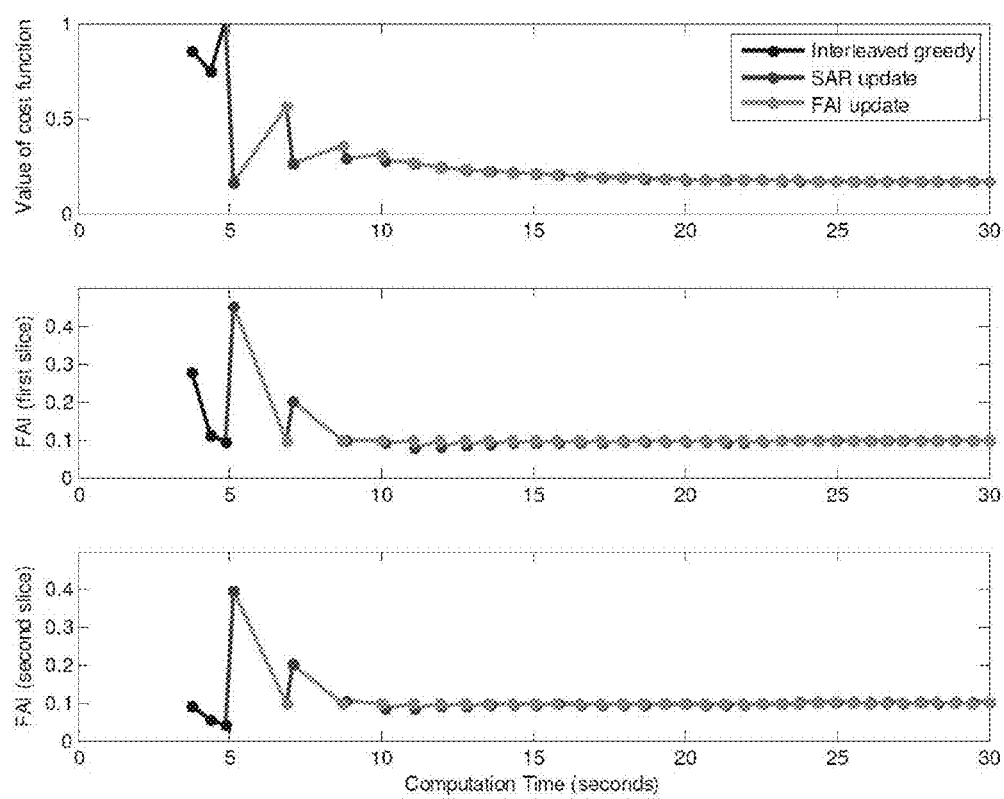
FIG. 5 illustrates the progress of cost function and FAI during optimization.

FIG. 5 illustrates the progress of cost function and FAI during optimization. The initialization step involves interpolating $B_1^+$ and $B_0$ maps onto the design grid to construct the system matrix and also preparing the SAR oracle from electric fields. The initial interleaved greedy optimization occurs in approximately one second and is used to select spokes locations and target phases such that the FAI tolerance constraint can be met. If the regularization parameter happens to be appropriate, no further MLS iterations will have to be performed. The start of the SAR aware portion of the optimization begins after 5 seconds. The SAR update serves to reduce SAR at the expense of possibly violating the FAI tolerance constraint. The FAI guarantees that the constraint is met exactly, at the expense of an increase in the value of the cost function. Convergence is reached when the SAR update produces negligible change to the FAI.

Discussion

IMPULSE provides a pulse design framework that leads to immense savings in computation time by eliminating the computationally expensive compression (VOP) step. In addition to this important benefit, IMPULSE is fundamentally superior to VOP-based methods as it avoids the overestimation cause by the compression and performs an optimization through an efficient oracle based algorithm that scales favorably with both number of slices and number of terms in the SAR estimate. This leads to improved performance of the optimization in terms of the degree of SAR reduction that is possible while still satisfying FAI constraints.

The first advantage is based on IMPULSE's ability to deal with non-convexities. Since the minimum SAR problem in its complete form is non-convex, it must be solved through an iterative method. Both the SQP and IMPULSE algorithms are composed of convex and non-convex subproblems. With the SQP method, the convex optimization step is a constrained minimization problem without any particularly efficient implementation. In contrast, with IMPULSE, the convex optimization step (SAR update) is an unconstrained minimization of a piecewise quadratic function that is solved efficiently through Kelley's cutting plane method. With the SQP method, the non-convex step consists of updates to the spokes locations and target phases for all slices. With IMPULSE, the non-convex FAI update requires updates to spokes locations and target phases like the SQP method but also includes a convex projection operation. Because this additional projection operation is efficient, the total duration of the non-convex step in IMPULSE is only slightly greater than the corresponding non-convex step with SQP. Therefore, each IMPULSE iteration is faster than each SQP iteration, allowing for more updates to spokes locations and target phases to be performed in a given amount time. For this reason, IMPULSE is a more efficient method for dealing with the non-convex aspects of the minimum SAR problem.

Another benefit of IMPULSE is the fact that the computation time per iteration is independent of the number of slices being designed, even when they are designed jointly. In the SAR update, increasing the number of slices does not increase computation time appreciably because the computation time for the sub-gradient oracle is relatively constant with respect to total number of slices. This is because a single matrix multiplication $R_{full}^T b_{full}$ is performed regardless of number of slices and the time for construction of $b_{full}$ increases only slightly with increasing number of slices. The FAI update can be completely parallelized across slices so computation time for the FAI update is also constant with respect to number of slices except for the small overhead of transferring data to each of the parallel workers. This ability to jointly optimize over arbitrarily many slices enables SAR hopping in an efficient time-frame.

The other fundamental advantage of IMPULSE is its scalability with number of terms in the cost function and therefore number of local SAR terms. Increasing the number of SAR terms increases the number of columns in $R_{full}$. When using a GPU optimized for matrix multiplication, this has negligible effect on the computation time of $R_{full}^T b_{full}$. This means that VOP compression of SAR matrices is no longer necessary, but it also means that arbitrarily many body models can be used for SAR estimation. It was shown that errors in the position of the body model as small as 1 cm in each direction can significantly affect the optimization and lead to a sub-optimal pulse. An approach to solving this would be to create a library of body models at various positions and choose from this "dense library" the subset of body models that are closest to the actual subject-on-the-table for the SAR estimate. This method was shown to provide a much better reduction of SAR than that obtained from a single mismatched body model. This approach works for both IMPULSE and SQP, but the fact that SQP scales unfavorably with the number of SAR terms makes such an approach impractical without IMPULSE.

Conclusion

This embodiment demonstrates the feasibility of, and validates using numerical simulations, the IMPULSE method as a novel pulse design algorithm with tangible benefits in terms of performance (improved ability to reduce SAR) and computational efficiency (elimination of a costly compression step and ability to incorporate non-convexities).

OTHER EMBODIMENTS

IMPULSE can be used for patient-specific SAR aware RF shimming which is a simpler cased of the complete pTx pulse design problem presented here. This simpler problem eliminates k-space optimization thus removing one degree of nonconvexity and also reduces the dimension of the optimization variable. The obvious tradeoff is a limit on the degree of excitation homogeneity that can be achieved compared to complete multi-subpulse parallel transmit.

IMPULSE can be generalized to arbitrary excitation k-space trajectories, target excitation patterns, or flip angle regimes. Since all aspects of the excitation accuracy of the pulse are encapsulated into the projection operation of the FAI update, modifying IMPULSE to fit a custom excitation scheme involves devising a method for projecting onto the feasible set based on the particular details of that excitation scheme. For example, with a kT-points trajectory still in the small-tip regime, this can be done trivially by changing the corresponding system matrix and target excitation pattern. For large tip angle pulses, this procedure will require more development, as the target excitation is no longer expressed as a matrix vector multiplication.

Improve the algorithm itself. More advanced forms of ADMM allow ρ to vary with iteration. This can improve the convergence properties and reduce sensitivity to a poor initial choice of ρ. The interleaved greedy algorithm for initialization may also have room for improvement by making that step SAR-aware while retaining computationally efficiency.

Provide other combinations of closely matched the body models to successfully and robustly estimate SAR for a patient. In addition to position, the effects of slight differences in the shape, composition and interior anatomical details of a patient and model could be investigated. The goal would be to create a library of different models that is sparse enough to be realizable while still allowing robust estimation of SAR in arbitrary subjects through the use of sufficiently many closely matched models from this library.

Use a real-time SAR estimation. This could be either through in-vivo SAR mapping or real-time body model creation and EM simulation. Such methods are still under development, [4,5] but once these have matured, can be combined with IMPULSE to make subject-specific and maximally accurate control of SAR in pTx a solved problem.

Figure 6:
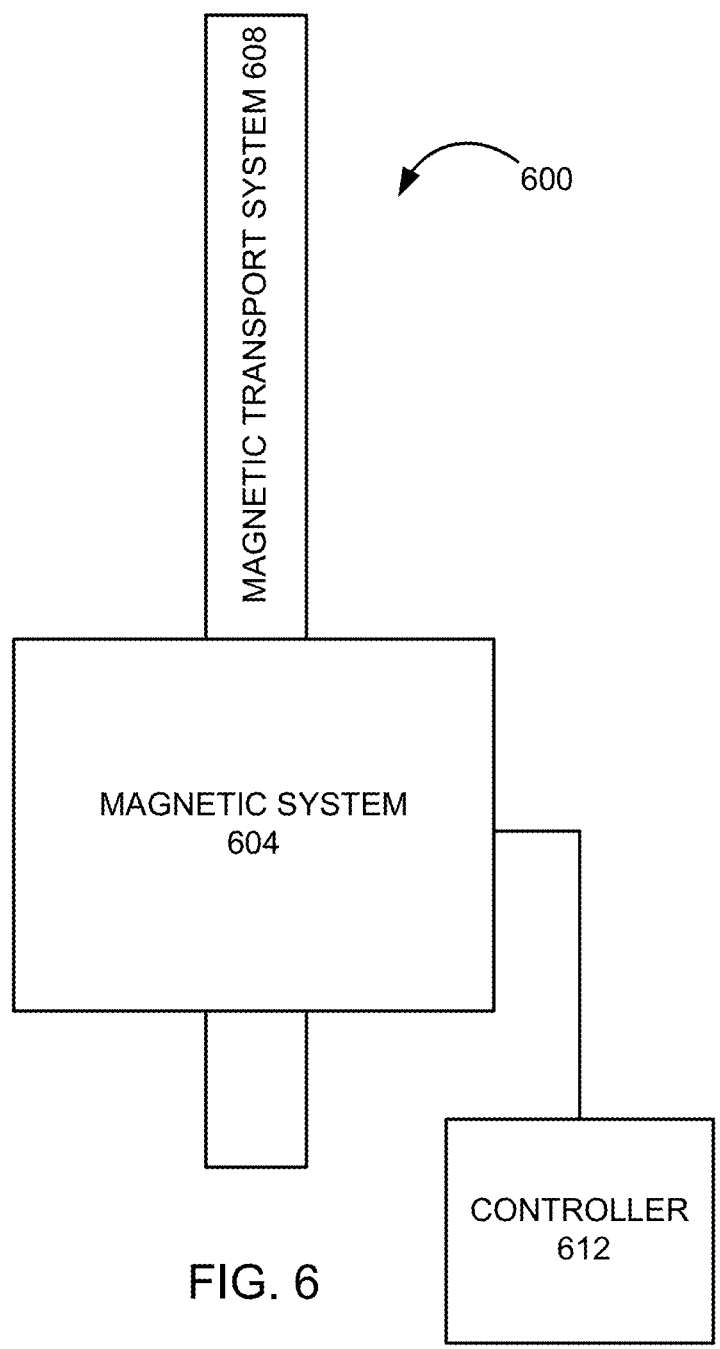
FIG. 6 is a schematic top view of a magnetic resonance imaging (MRI) system that may be used in an embodiment of the invention.

To further facilitate understanding of the invention, FIG. 6 is a schematic top view of a magnetic resonance imaging (MRI) system 600 that may be used in an embodiment of the invention. The MRI system 600 comprises a magnet system 604, a patient transport table 608 connected to the magnet system, and a controller 612 controllably connected to the magnet system. In one example, a patient (subject) would lie on the patient transport table 608 and the magnet system 604 would pass around the patient. The controller 612 would control magnetic fields and radio frequency (RF) signals provided by the magnet system 604 and would receive signals from detectors in the magnet system 604.

Figure 7:
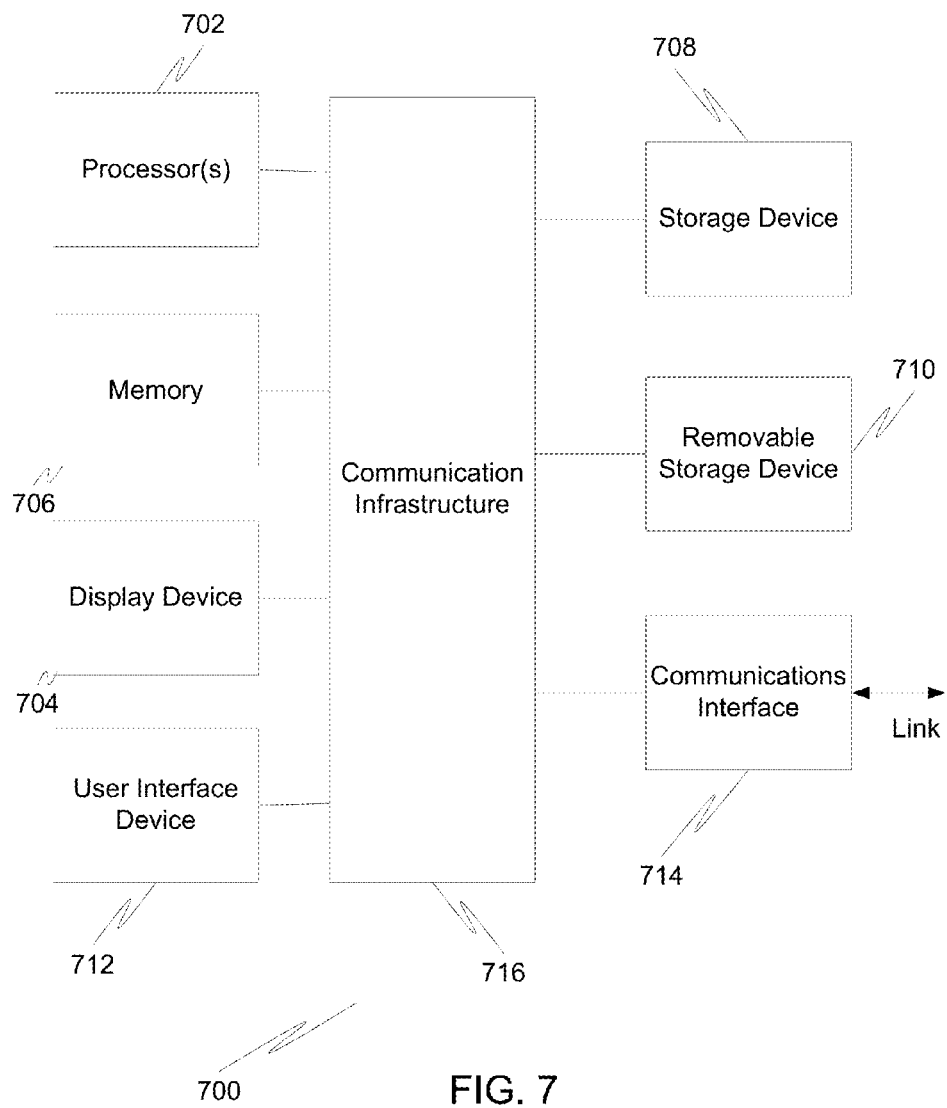
FIG. 7 is a high level block diagram showing a computer system.

FIG. 7 is a high level block diagram showing a computer system 700, which is suitable for implementing the controller 612 used in embodiments of the present invention. The computer system may have many physical forms ranging from an integrated circuit, a printed circuit board, and a small handheld device up to a super computer. The computer system 700 includes one or more processors 702, and further can include an electronic display device 704 (for displaying graphics, text, and other data), a main memory 706 (e.g., random access memory (RAM)), storage device 708 (e.g., hard disk drive), removable storage device 710 (e.g., optical disk drive), user interface devices 712 (e.g., keyboards, touch screens, keypads, mice or other pointing devices, etc.), and a communication interface 714 (e.g., wireless network interface). The communication interface 714 allows software and data to be transferred between the computer system 700 and external devices via a link. The system may also include a communications infrastructure 716 (e.g., a communications bus, cross-over bar, or network) to which the aforementioned devices/modules are connected.

Information transferred via communications interface 714 may be in the form of signals such as electronic, electromagnetic, optical, or other signals capable of being received by communications interface 714, via a communication link that carries signals and may be implemented using wire or cable, fiber optics, a phone line, a cellular phone link, a radio frequency link, and/or other communication channels. With such a communications interface, it is contemplated that the one or more processors 702 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 8:
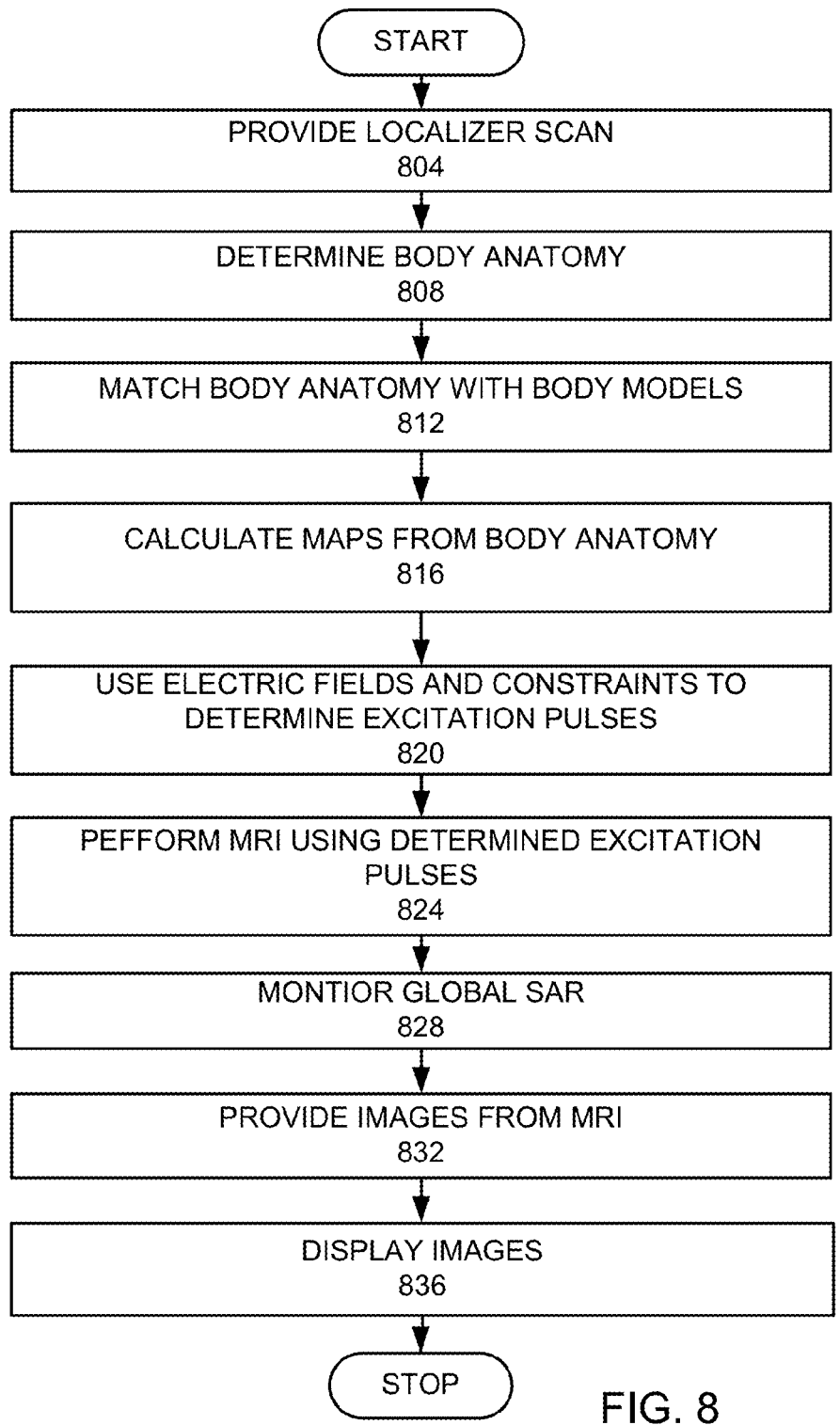
FIG. 8 is a flow chart of a process used in an embodiment of the invention.

FIG. 8 is a flow chart of a process used in an embodiment of the invention. For a subject placed in the MRI system 600, a localizer scan of the subject is provided (step 804). A localizer scan is defined as a relatively low-resolution scan not utilizing pTx functionality meant to determine morphology and position of the anatomy of interest and not exceeding few seconds of scan time.

Body type anatomy is determined from the localizer scan (step 808). This will include positioning of the body with respect to the RF coil as well as dimensions of the anatomy. In the first embodiment, the patient anatomy is matched with a single closely-matched body model. In a second embodiment, the body type anatomy is match with multiple body models each a certain degree of mismatch with the patient. In a third embodiment no body model matching is performed and a tissue properties map and body model is constructed through segmentation of the localizer scan and electric fields are simulated on this custom body model [6]. In a fourth embodiment, the custom body model is created not through segmentation but through warping of an existing body model based on the localizer scan [7]. In the fifth embodiment, no body models are used and SAR is measured in-vivo [4,5].

In one embodiment, the electric fields of one or more of the body type models have been precalculated through and electromagnetic simulation with a realistic RF coil model. The precalculation of the electric fields allows for a faster process, by eliminating the time required to calculate electric fields for each body model. However, due to the unique ability of IMPULSE to bypass the time-consuming VOP compression step, another embodiment is also possible wherein the electric fields for a body type model are calculated when needed through electrical properties tomography [4] or thermoacoustic SAR mapping [5].

$B_1^+$ and $B_o$ maps are calculated from the body anatomy (step 816). $B_1^+ \cdot B_1+$ and $B_o$ mapping is done on the scanner through established methods such as Bloch-Siegert and is independent of electric field calculation.

Electric fields from at the at least one body model and constraints are used to simultaneously determine a plurality of excitation pulses for a pTx (step 820). In an embodiment, the electric fields are determined as an optimization problem with a single objective term consisting of all time-averaged quantities including local SAR, global SAR, and average power and constraints on instantaneous quantities including flip angle inhomogeneity resulting from each pulse and instantaneous power applied to each channel. In this embodiment, local SAR matrices at all voxels are included in the objective term without need for compression.

MRI is performed on the subject using the determined excitation pulses (step 824). Global SAR is monitored in real time to ensure all time-averaged constraints are satisfied simultaneously (step 828). Images are provided from the MRI (step 832). The MRI process acquires a readout. The readout data is used to create MRI images. The images are displayed (step 836).

In an embodiment where more than one body model is used for SAR estimation the SAR matrices are concatenated from the voxels across all of the matched body models. In an embodiment of the invention, only the magnitude of the excitation pulses and not the phase is of interest. In an embodiment, the optimization problems is decomposed with the alternating direction method of multipliers algorithm resulting in two subproblems to be solved iteratively. In an embodiment, a first subproblem consists of an unconstrained minimization of a piecewise positive semidefinite function. In an embodiment, a second subproblem consists of a projection operation onto the nonconvex set of feasible pulses. In an embodiment, the first subproblem is solved with Kelley's cutting plane algorithm, as discussed above. In an embodiment, the projection operation is performed in parallel for each RF pulse. In an embodiment, the nonconvex projection operation is accomplished through sequential convex projections onto ellipsoids with fixed k-space locations and target phases. In an embodiment the $B_1^+$ and $B_o$ mapping is performed in parallel. In an embodiment, the RF pulse design is performed in parallel with non-pTx scanning. Preferably, the MRI system provides a field of at least 7 Tesla.

APPENDIX

Appendix A: Derivation of the Alternating Direction Method of Multipliers

To solve a problem of the form:

MINIMIZE $g(y)+h(z)$      Problem 1:

SUBJECT TO $y=z$

This is equivalent to solving:

MAXIMIZE $v(w)=\min_{y,z}(g(y)+h(z)+w^T(y-z))$      Problem 2:

The reasoning for this equivalency is that for a given w, v(w) will give a lower bound on the optimal value for Problem 1. The maximum of this lower bound over all values of w will give the solution of Problem 1. The constraint y=z is implicitly satisfied by solving Problem 2 since if y≠z then it will always be possible to find some w such that v(w) is infinity. Problem 2 is called the dual problem of Problem 1 (which is called the primal problem) and solving this dual problem is a standard approach for equality constrained optimization. y and z are called primal variables and w is called the dual variable or Lagrange multiplier (hence the name method of multipliers). To solve Problem 2, a gradient ascent type method can be used with basic idea of computing the gradient (or technically subgradient if nondifferentiable) of the dual cost function with respect to the dual variable w and iteratively updating w with a step in the positive gradient direction. The gradient (at iteration k) can be computed in a two step manner:

1. $(y^{(k+1)},z^{(k+1)})=\mathrm{argmin}_{y,z}(g(y)+h(z)+w^{(k)T}(y-z))$
2. $\nabla v(w^{(k)})=y^{(k+1)}-z^{(k+1)}$ Then the update of w is $$w^{(k+1)}=w^{(k)}+\alpha(y^{(k+1)}-z^{(k+1)})$$

Where $\alpha$ is the step size.

Since the expression $g(y)+h(z)+w^{(k)T}(y-z)$ is completely separable in y and z, $(y^{(k+1)},z^{(k+1)})=\mathrm{argmin}_{y,z}(g(y)+h(z)+w^{(k)T}(y-z))$ can be easily decomposed into $y^{(k+1)}=\mathrm{argmin}_y(g(y)+w^{(k)T}y)$ and $z^{(k+1)}=\mathrm{argmin}_z(h(z)+w^{(k)T}z)$. Unfortunately the algorithm as stated has poor convergence properties. This can be improved by adding a penalty or regularization term to the objective of problem 1:

$$\text{MINIMIZE } g(y) + h(z) + \frac{\rho}{2}\|y-z\|_2^2$$

$$\text{SUBJECT TO } y = z$$

This is equivalent to the previous problem since when the constraint is met, the penalty is 0. The algorithm is now:

1.

$$(y^{(k+1)}, z^{(k+1)}) = \mathrm{argmin}_{y,z}\left(g(y) + h(z) + w^{(k)T}(y-z) + \frac{\rho}{2}\|y-z\|_2^2\right)$$

2.

$$\nabla v(w^{(k)}) = y^{(k+1)} - z^{(k+1)}$$

The optimal step size can be shown to be $\rho$ so the update of w is $$w^{(k+1)}=w^{(k)}+\rho(y^{(k+1)}-z^{(k+1)})$$

Unfortunately, because of the penalty term, the first step is no longer separable with y and z. Therefore, the joint minimization in step 1 cannot be accomplished exactly in a sequential way. Nonetheless, by performing the updates sequentially (or in alternating directions) and then iterating convergence can be shown to occur (even though at each iteration the exact gradient is not found so the direction of ascent is not the steepest). The $\rho$ parameter can be tuned to optimize the convergence rate. So the algorithm is:

1.

$$y^{(k+1)} = \mathrm{argmin}_y\left(g(y) + h(z^{(k)}) + w^{(k)T}(y-z^{(k)}) + \frac{\rho}{2}\|y-z^{(k)}\|_2^2\right) =$$

$$\mathrm{argmin}_y\left(g(y) + w^{(k)T}y + \frac{\rho}{2}\|y\|_2^2 - \rho y^T z^{(k)}\right) =$$

$$\mathrm{argmin}_y\left(g(y) + \frac{\rho}{2}\|y\|_2^2 + \rho y^T\left(\frac{1}{\rho}w^{(k)} - z^{(k)}\right)\right) =$$

$$\mathrm{argmin}_y\left(g(y) + \frac{\rho}{2}\left\|y + \left(\frac{1}{\rho}w^{(k)} - z^{(k)}\right)\right\|_2^2\right)$$

2.

$$z^{(k+1)} = \mathrm{argmin}_z\left(g(y^{(k+1)}) + h(z) + w^{(k)T}(y^{(k+1)} - z) + \frac{\rho}{2}\|y^{(k+1)} - z\|_2^2\right) =$$

$$\mathrm{argmin}_z\left(h(z) + u^{(k)T}z + \frac{\rho}{2}\|z\|_2^2 - \rho z^T y^{(k+1)}\right) =$$

$$\mathrm{argmin}_z\left(h(z) + \frac{\rho}{2}\|z\|_2^2 + \rho z^T\left(\frac{1}{\rho}w^{(k)} - y^{(k+1)}\right)\right) =$$

-continued $$\text{argmin}_z \left( h(z) + \frac{\rho}{2} \left\| z + \left( \frac{1}{\rho} w^{(k)} - y^{(k+1)} \right) \right\|_2^2 \right)$$

3.

$$w^{(k+1)} = w^{(k)} + \rho(y^{(k+1)} - z^{(k+1)})$$

For simplicity define $$u = \frac{1}{\rho} w$$

so the complete ADMM algorithm for each iteration is:

1. $\text{argmin}_y \left( g(y) + \frac{\rho}{2} \| y + u^{(k)} - z^{(k)} \|_2^2 \right)$ 2. $\text{argmin}_z \left( h(z) + \frac{\rho}{2} \| z + u^{(k)} - y^{(k+1)} \|_2^2 \right)$ 3. $u^{(k+1)} = u^{(k)} + y^{(k+1)} - z^{(k+1)}$ While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

REFERENCES

The following references are incorporated by reference for all purposes.

[1] Grissom W A, Khalighi M M, Sacolick L I, Rutt B K, Vogel M W. "Small tip angle spokes pulse design using interleaved greedy and local optimization methods," Magn Reson Med 2012; 68:1553-1562.

[2] KRZYSZTOF C. KIWIEL "A Method for Solving Certain Quadratic Programming Problems Arising in Nonsmooth Optimization," IMA J Numer Anal (1986) 6 (2): 137-152

[3] Y. N. Kiseliov, "Algorithms of projection of a point onto an ellipsoid," Lithuanian Math. J., vol. 34, no. 2, pp. 141-159, 1994.

[4] X. Zhang, S. Schmitter, P. Van de Moortele, J. Liu, and B. He, "From complex B1 mapping to local SAR estimation for human brain MR imaging using multi-channel transceiver coil at 7 T," IEEE Trans. Med. Imag., vol. 32, no. 6, pp. 1058-1067, 2013.

[5] Winkler S A, Picot P, Thornton M, Rutt B K, "Direct SAR Mapping by Thermoacoustic Imaging: A Feasibility Study" Proceedings International Society for Magnetic Resonance in Medicine, Milan, Italy; May 2014

[6] Angel Torrado-Carvajal, Juan A. Hernandez-Tamames, Joaquin L. Herraiz, Yigitcan Eryaman, Elfar Adalsteinsson, Lawrence L. Wald, and Norberto Malpica "Automatic Segmentation Pipeline for Patient-Specific MRI Tissue Models"

[7] Leeor Alon, Cem M. Deniz, Giuseppe Carluccio, Mary Bruno, Daniel K. Sodickson, and Christopher C. Collins "A Method For Subject-Specific Body Model Generation using Affine And Non-Linear Transformations"

What is claimed is:

1. A method for providing an image of a subject in a magnetic resonance imaging MRI system with parallel transmission (pTx), comprising:
   a) providing a localizer scan of the subject;
   b) determining body anatomy from the localizer scan;
   c) matching the body anatomy with at least one body model of a plurality of body models;
   d) calculating $B_1^+$ and $B_0$ maps from the body anatomy;
   e) using electric fields from the at least one body model and constraints to simultaneously determine a plurality of excitation pulses for a pTx performed as an optimization problem with a single objective term consisting of all time-averaged quantities including local SAR, global SAR, and average power and constraints on instantaneous quantities including flip angle inhomogeneity resulting from each pulse and instantaneous power applied to each channel, wherein local SAR matrices at all voxels are included in the objective term without compression;
   f) performing MRI on the subject using the determined excitation pulses;
   g) monitoring global SAR in real time to ensure all time-averaged constraints are satisfied simultaneously; and
   h) providing an image from the performing the MRI on the subject and monitoring the global SAR in real time.

2. The method, as recited in claim 1, wherein more than one body model is used for SAR estimation, performed by concatenating SAR matrices from the voxels across all body models.

3. The method, as recited in claim 1, wherein only the magnitude of excitation is determined and the phase of excitation is not determined.

4. The method, as recited in claim 1, wherein flip angle inhomogeneity is nonconvex with freedom in choice of spokes locations and target phase.

5. The method, as recited in claim 1, wherein the optimization problem is decomposed into two subproblems to determine the pulses iteratively.

6. The method, as recited in claim 5, wherein a first subproblem of the two subproblems consists of an unconstrained minimization of a piecewise positive semidefinite function.

7. The method, as recited in claim 6, wherein a second subproblem of the two subproblems consists of a projection operation onto a nonconvex set of feasible pulses.

8. The method, as recited in claim 6, wherein the first subproblem is solved with Kelley's cutting plane algorithm.

9. The method, as recited in claim 8, wherein a subgradient and value of the time-averaged cost function in each iteration of Kelley's cutting plane algorithm is computed with a vectorized oracle.

10. The method, as recited in claim 9, wherein the vectorized oracle exists on a GPU for additional acceleration.

11. The method, as recited in claim 7, wherein the projection operation is performed in parallel for each RF pulse.

12. The method, as recited in claim 7, wherein the nonconvex projection operation is accomplished through sequential convex projections onto ellipsoids with fixed k-space locations and target phases.

13. The method, as recited in claim 1, wherein the step of calculating $B_1^+$ and $B_0$ maps from the body anatomy is performed on a scanner while the step of matching the body anatomy with at least one body model of a plurality of body models is computed on a workstation simultaneously in parallel.

14. The method, as recited in claim 1, wherein RF pulse design is performed in parallel with non-pTx scanning.

15. The method, as recited in claim 1, wherein electric fields of at least one body model of the plurality of body models has been precalculated, and wherein using the electric fields, comprises using the precalculated electric fields of the at least one matched body model.

* * * * *